(12) United States Patent
Wan Fong et al.

(10) Patent No.: US 7,699,784 B2
(45) Date of Patent: Apr. 20, 2010

(54) SYSTEM FOR DETECTING AND MONITORING VITAL SIGNS

(75) Inventors: David Kim Soui Wan Fong, St-Romuald (CA); Jean-Paul Dionne, Lévis (CA)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 11/773,714

(22) Filed: Jul. 5, 2007

(65) Prior Publication Data
US 2008/0005838 A1    Jan. 10, 2008

Related U.S. Application Data

(60) Provisional application No. 60/818,699, filed on Jul. 5, 2006.

(51) Int. Cl.
*A61B 5/08*    (2006.01)
*A61B 5/02*    (2006.01)
*A47B 71/00*   (2006.01)

(52) U.S. Cl. .................. 600/481; 600/484; 600/500; 600/529; 600/534

(58) Field of Classification Search .................. 600/534
See application file for complete search history.

(56) References Cited

U.S. PATENT DOCUMENTS

| 4,595,016 | A | 6/1986 | Fertig et al. |
| 4,657,026 | A | 4/1987 | Tagg |
| 5,184,112 | A | 2/1993 | Gusakov |
| 5,276,432 | A | 1/1994 | Travis |
| 5,571,142 | A | 11/1996 | Brown et al. |
| 5,590,650 | A | 1/1997 | Genova |
| 5,620,003 | A * | 4/1997 | Sepponen .................... 600/527 |
| 5,684,460 | A | 11/1997 | Scanlon |
| 6,280,392 | B1 | 8/2001 | Yoshimi et al. |
| 6,374,140 | B1 * | 4/2002 | Rise ............................ 607/45 |
| 6,450,957 | B1 | 9/2002 | Yoshimi et al. |
| 6,546,813 | B2 | 4/2003 | Hubbard, Jr. |
| 6,547,743 | B2 * | 4/2003 | Brydon ....................... 600/534 |

(Continued)

FOREIGN PATENT DOCUMENTS

JP    2000175904 A    6/2000

(Continued)

OTHER PUBLICATIONS

J.C. Barbenal et al., "Monitoring the mobility of patients in bed", Medical and Biological Engineering and Computing, pp. 466-468, Sep. 1985.

(Continued)

*Primary Examiner*—Patricia C Mallari
(74) *Attorney, Agent, or Firm*—Van Dyke, Gardner, Linn & Burkhart, LLP

(57) ABSTRACT

A system and method for determining and monitoring various characteristics of a patient positioned on a patient support apparatus, such as a bed, stretcher, or cot, is disclosed. The system and method involve monitoring the forces exerted by the patient on one or more force sensors, which may be load cells on the support apparatus. These force sensors will detect vibrations that correspond to various conditions of the patient, including the patient's heart rate, breathing rate, and/or the seizure status of a patient. These vibrations may be analyzed, such as by Fast Fourier Transforms, in order to determine the various conditions of the patient.

39 Claims, 17 Drawing Sheets

U.S. PATENT DOCUMENTS

| | | | |
|---|---|---|---|
| 6,984,207 B1 * | 1/2006 | Sullivan et al. | 600/301 |
| 7,077,810 B2 | 7/2006 | Lange et al. | |
| 7,314,451 B2 | 1/2008 | Halperin et al. | |
| 2004/0087865 A1 | 5/2004 | Kelly | |
| 2004/0194220 A1 * | 10/2004 | Price et al. | 5/713 |
| 2006/0028350 A1 | 2/2006 | Bhai | |
| 2006/0100534 A1 | 5/2006 | Colombo et al. | |
| 2006/0129047 A1 | 6/2006 | Ruotoistenmaki | |
| 2007/0118054 A1 | 5/2007 | Pinhas et al. | |
| 2007/0149883 A1 | 6/2007 | Yesha | |

FOREIGN PATENT DOCUMENTS

| | | | |
|---|---|---|---|
| JP | 2000316915 A | | 11/2000 |
| JP | 2001000401 A | | 1/2001 |
| JP | 2001037821 A | | 2/2001 |
| JP | 2004180804 | | 7/2004 |
| JP | 2005013259 | | 1/2005 |
| WO | WO 2005/074379 | * | 8/2005 |

OTHER PUBLICATIONS

Charles F. Babbs, et al., "A Pressure-Sensitive Mat for Measuring Contact Pressure Distributions . . . ", Biomedical Instrumentation and Technology, pp. 363-370, Sep./Oct. 1990.

The Search Report for PCT application PCT/US07/72854, which is the foreign counterpart to the present application.

The Written Opinion of the International Searching Authority for PCT application PCT/US07/72854, which is the foreign counterpart to the present application.

* cited by examiner

US 7,699,784 B2

SYSTEM FOR DETECTING AND MONITORING VITAL SIGNS

CROSS-REFERENCE TO RELATED APPLICATIONS

This application claims priority to commonly-assigned, U.S. provisional application Ser. No. 60/818,699 filed Jul. 5, 2006 by applicant David Wan Fong entitled System for Detecting and Monitoring Vital Signs, the complete disclosure of which is hereby incorporated herein by reference.

BACKGROUND OF THE INVENTION

The present invention relates to patient support apparatuses, such as beds, stretchers, cots, or the like, and more particularly to patient support apparatuses that monitor one or more conditions of the patient while the patient is positioned on the support apparatus.

A patient's health status is typically evaluated by reference to a plurality of vital signs, such as a pulse rate and breathing rate. When these vital signs fall below or rise above normal readings, a patient is usually in distress and requires quick attention by healthcare professionals. It is therefore desirable for health care professionals to know these vital sign readings.

SUMMARY OF THE INVENTION

Accordingly, the present invention provides an improved system for monitoring and gathering important information about a patient, such as the patient's vital signs and/or whether or not the patient is experiencing a seizure or not. The systems and methods of the present invention allow this information to be monitored and collected in a non-intrusive manner, without the need for attending personnel to utilize special instruments to measure this information, and without the need for attending personnel to be physically located in the same room as the patient. The systems and methods of the present invention also allow the information to be collected and monitored over long periods of time without requiring any work from attending personnel. The systems and methods of the present invention thereby overcome several disadvantages of prior art systems for measuring pulse rates and breathing rates, which have been intrusive to the patient and have required active participation by the attending personnel.

According to one aspect of the present invention, a patient support apparatus is provided that includes a support, at least one force sensor, and a controller. The support is adapted to at least partially support the weight of a patient. The force sensor detects a force exerted from the support onto the force sensor. The force sensor outputs a signal corresponding to the force. The controller is in communication with the force sensor and is adapted to determine from the signal either a breathing rate, a heart rate, or both, for a patient lying on the support deck.

According to another aspect of the present invention, a method for collecting data about a patient is provided. The method includes providing a support and a force sensor wherein the support supports at least a portion of a patient's weight, and the force sensor senses a force exerted by the support on the force sensor. The force sensor generates a signal corresponding to the force, and a Fast Fourier Transform is performed on the signal. The Fast Fourier Transform is then analyzed.

According to still another aspect of the present invention, a method of analyzing the forces exerted by a patient onto a patient support in communication with a force sensor wherein the force sensor outputs a signal corresponding to the forces is provided. The method includes processing the signal to produce a processed output, as well as using a second sensor different from the force sensor to determine one of the patient's breathing rate and heart rate. Thereafter, a determination is made of a correlation between the patient's breathing rate and/or heart rate as determined by the second sensor. The correlation may be stored in an electronic memory for future use in situations where the second sensor is not used.

According to other aspects of the present invention, the signals from the force sensor may be analyzed to determine whether a patient is experiencing a seizure or not, in addition to, or separately from, the determinations made regarding the breathing rate and/or heart rate of the patient. The breathing rate may be determined by determining a peak frequency in the Fast Fourier Transform, and the pulse rate may be determined by analyzing one or both of a pair of peak frequencies in the Fast Fourier Transform having higher frequency values than the peak frequency used to determine the breathing rate. The controller may be in communication with an alarm that it activates if the breathing rate or pulse rate meet a specified criteria, or if a seizure is detected. The alarm may be located at a room outside the room in which the patient support apparatus is located. The criteria for setting off the alarm may also be adjustable by an attendant so that specific monitoring conditions can be tailored to individual patients.

DETAILED DESCRIPTION OF THE INVENTION

Figure 1:
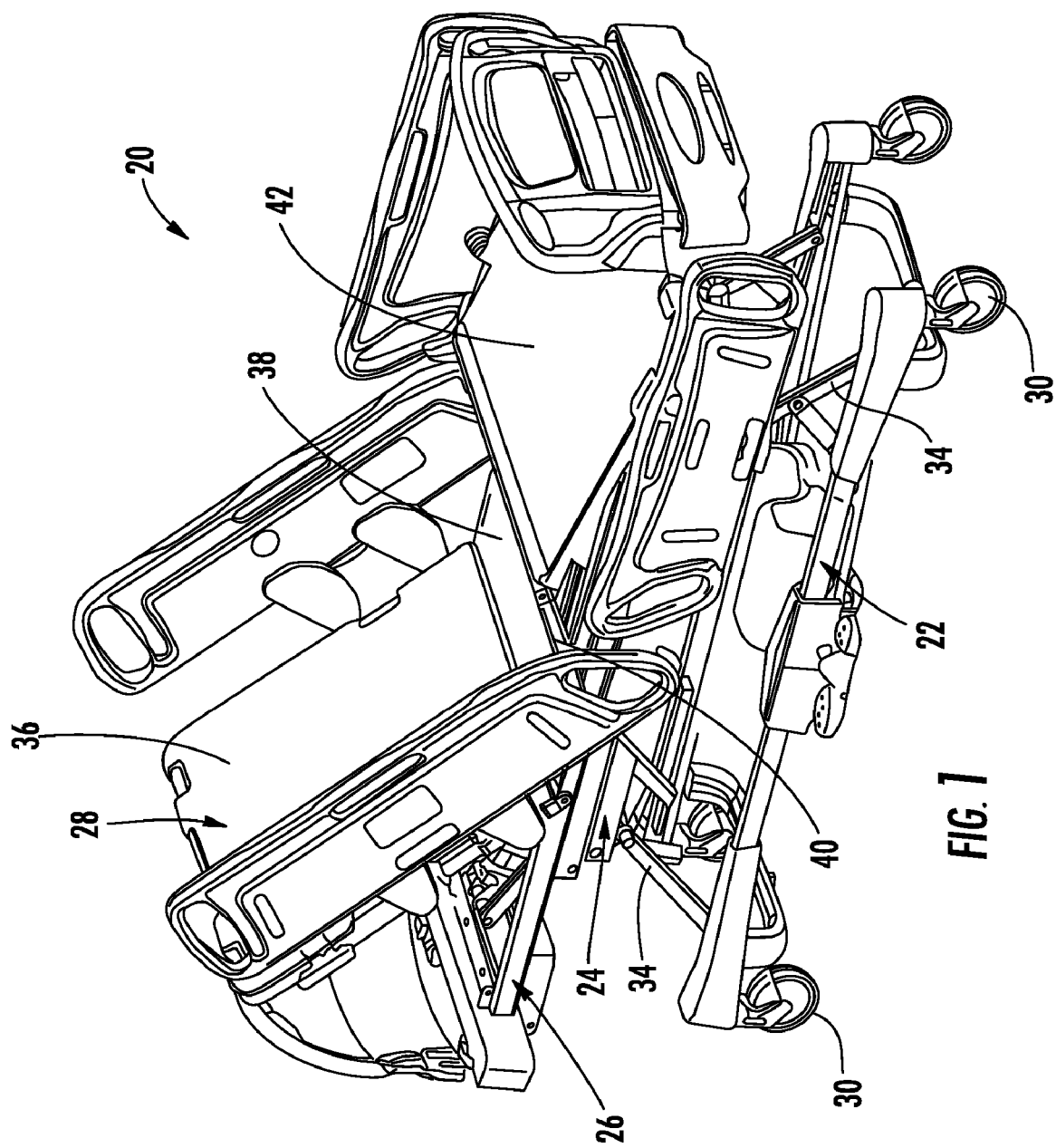
FIG. 1 is a perspective view of a patient support apparatus according to one aspect of the present invention shown with a head section of a patient support deck pivoted to an elevated position.
Figure 2:
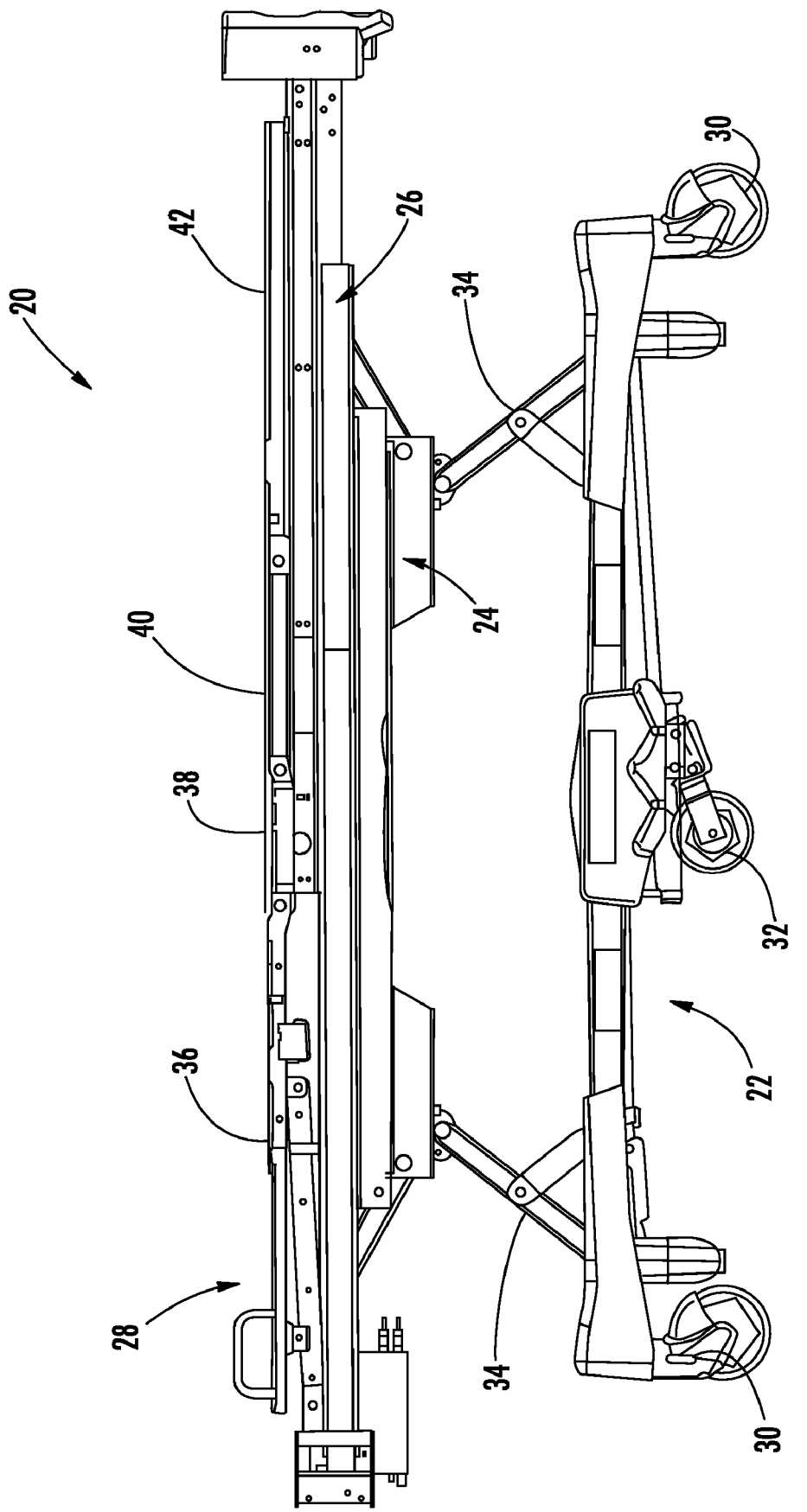
FIG. 2 a side, elevational view of the patient support apparatus of FIG. 1 shown with the patient support deck pivoted to a horizontal orientation and with various components removed for clarity, such as the side rails and head rails.

The present invention will now be described with reference to the accompanying drawings wherein the reference numerals appearing in the following written description correspond to like-numbered elements in the several drawings. The methods and systems of the present invention may be incorporated into any known bed, stretcher, cot, or other type of patient support apparatus having one or more force sensors, as will be discussed in greater detail below. One such patient support apparatus that may incorporate the systems and methods of the present invention is patient support apparatus 20, depicted in FIG. 1. Patient support apparatus 20 includes a base 22, an intermediate frame 24, a load frame 26, and a support deck 28. Base 22 may include one or more castered wheels 30 and a fifth wheel 32 that is moveable between a raised position out of contact with the ground and a lowered position in contact with the ground, the latter position facilitating steering of patient support apparatus 20. Intermediate frame 24 is supported on base 22 by way of a pair of lift arms 34. Lift arms 34 are pivotably coupled to base 22 such that their pivoting enables the height and angular orientation of intermediate frame 24 to be adjusted with respect to base 22. Load frame 26 is supported on intermediate frame 24 and load frame 26 supports support deck 28. Support deck 28 is adapted to support a mattress or other type of sleep surface that comfortably supports a patient. Support deck 28 includes a head section 36, a seat section 38, a thigh section 40, and foot section 42. Sections 36, 38, 40, and 42 are all pivotably coupled to each other and/or load frame 26 such that they can articulate between the flat, horizontal orientation of FIG. 2 and various raised orientations, one of which is illustrated in FIG. 1. Further details of the construction of patient support apparatus 20 can be found in commonly-assigned, co-pending U.S. application Ser. No. 11/362,543 filed Feb. 23, 2006 by applicants Guy Lemire et al., and entitled Hospital Patient Support, the complete disclosure of which is hereby incorporated herein by reference.

Figure 3:
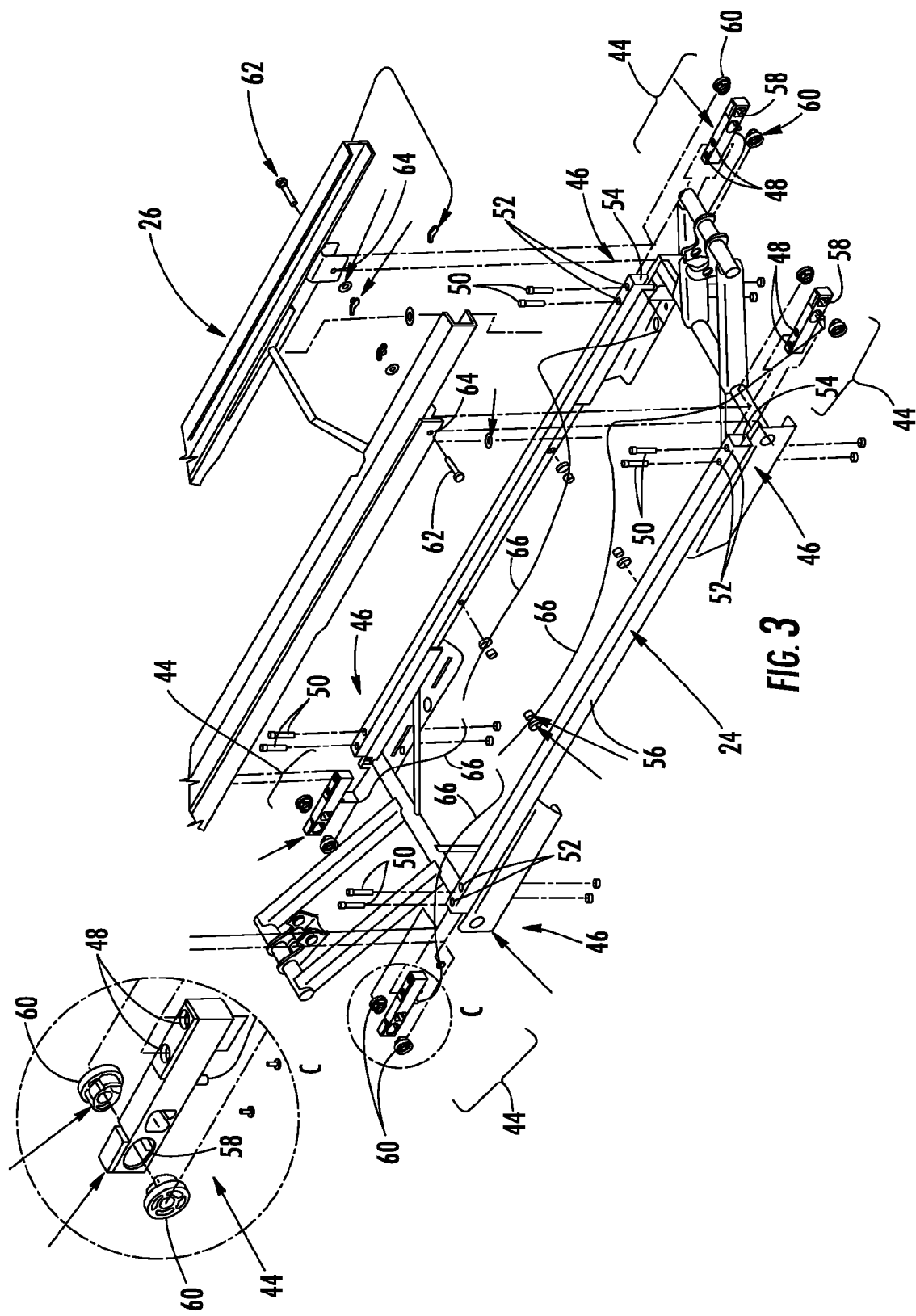
FIG. 3 is a perspective view of an intermediate frame of the patient support apparatus of FIG. 1 illustrating the location of four load cells.
Figure 4:
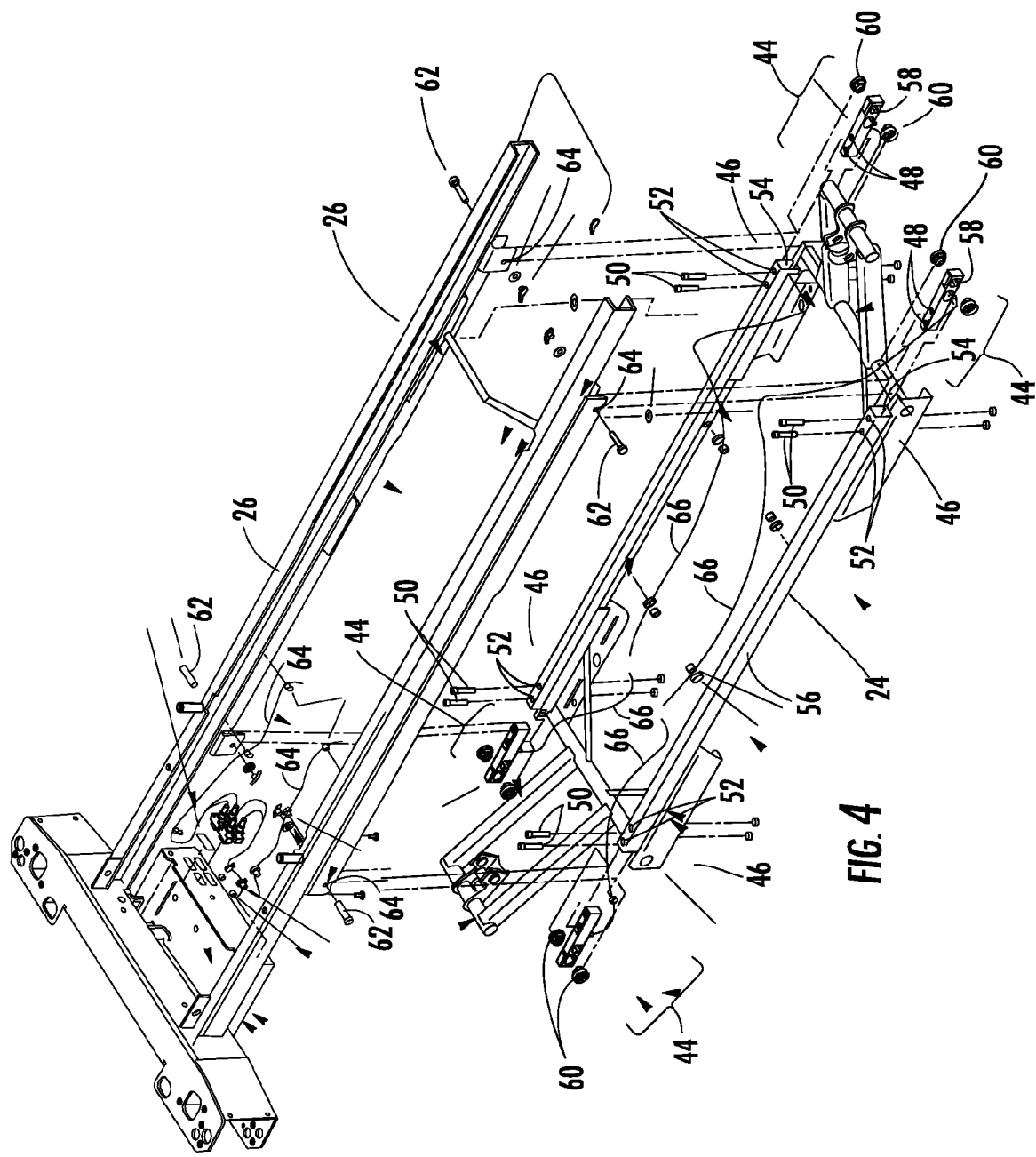
FIG. 4 is a perspective, exploded view similar to that of FIG. 3 showing a load frame positioned above the intermediate frame.

Patient support apparatus 20 includes a plurality of force sensors 44 positioned between intermediate frame 24 and load frame 26 (FIGS. 3-4). Force sensors 44 may be any type of sensors that are capable of detecting the forces exerted by load frame 26 onto intermediate frame 24. In one embodiment, force sensors 44 may be any type of conventional load cell, such as, but not limited to, hydraulic load cells, pneumatic load cells, mechanical load cells, strain gauge load cells, bending beam load cells, shear beam load cells, canister load cells, ring and pancake load cells, button and washer load cells, helical load cells, fiber optic load cells, and piezoelectric load cells.

Force sensors 44 are positioned at each of four corners 46 of intermediate frame 24 (FIGS. 3-4). Force sensors 44 each include a pair of vertical fastener apertures 48 that receive corresponding fasteners 50, such as, but not limited to, screws and/or bolts and nuts. Fasteners 50 also pass through a pair of fastener apertures 52 on intermediate frame 24, thereby securing force sensors 44 to intermediate frame 24. Force sensors 44 are dimensioned to fit within a rectangular opening 54 defined at each end of a longitudinal support rail 56. Intermediate frame 24 includes a pair of longitudinal support rails 56 that are parallel to each other and positioned along the sides of patient support apparatus 20.

In the illustrated embodiment, each force sensor 44 includes an aperture 58 having a generally horizontal axis. A pair of collars 60 are inserted into either side of aperture 58 and positioned therein. A fastener 62, such as, but not limited to, a screw and/or a bolt and nut, is inserted through a horizontal fastener aperture 64 positioned generally on the underside of load frame 26. Fastener 62 also passes through collars 60, thereby securing load frame 26 to intermediate frame 24. Load frame 26 is supported on intermediate frame 24 only at the corners 46 of intermediate frame 24. More specifically, load frame 26 is completely supported on intermediate frame 24 by way of force sensors 44. Thus, the entire weight of load frame 26, as well as all the other structures supported by load frame 26 (including any patient on support deck 28) will be measured by force sensors 44. Force sensors 44 can thus be used to measure the weight of a patient positioned on support deck 28 by simply subtracting the tare weight of the non-patient items from the gross weight measured by the force sensors 44. The resulting net weight is the weight of the patient.

Figure 5:
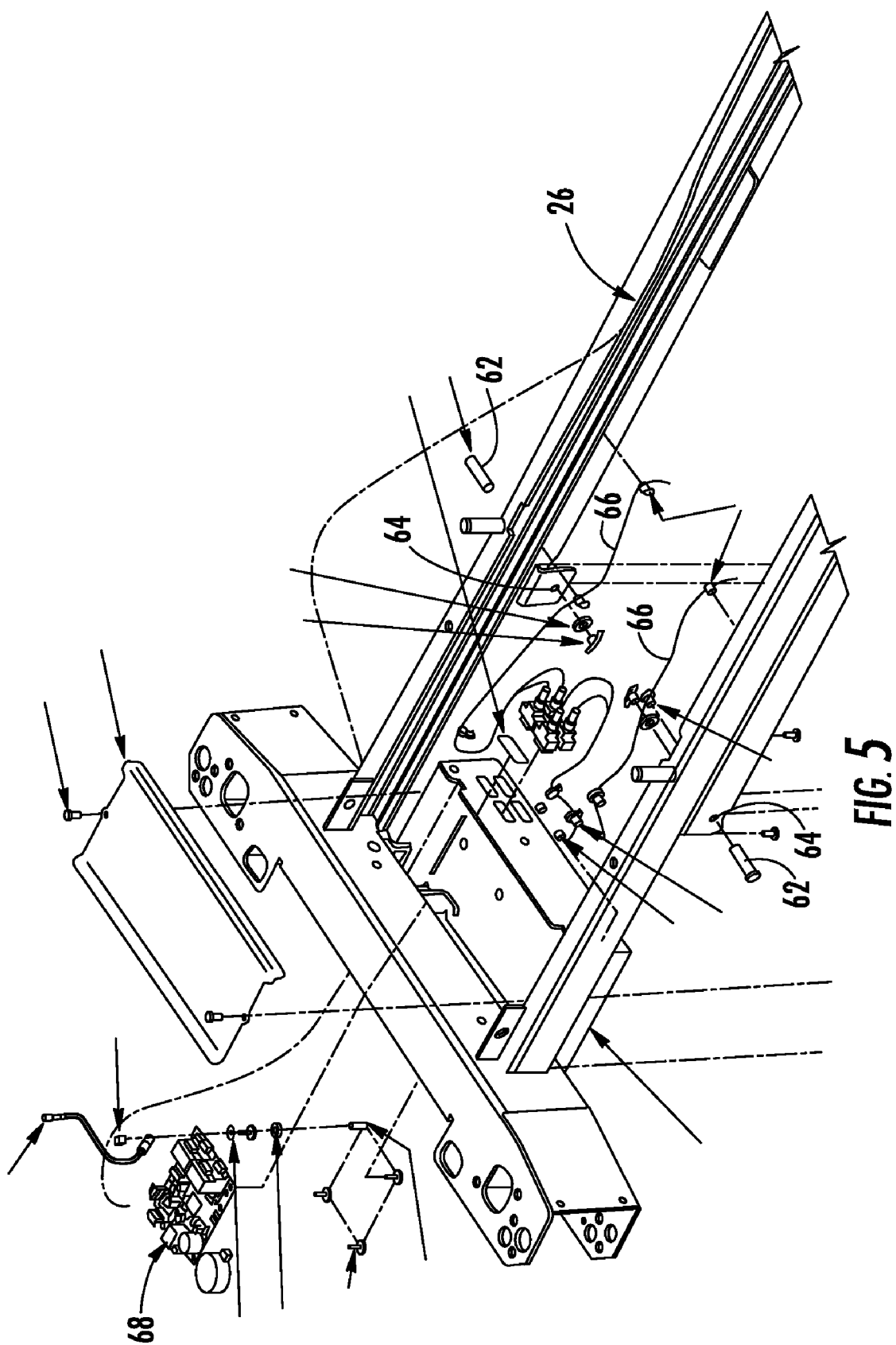
FIG. 5 is a perspective view of a portion of the load frame and intermediate frame of FIGS. 3 and 4 illustrating an electronic controller.

Each of the force sensors 44 includes a cable 66 over which electrical signal indicative of the forces sensed by force sensors 44 are transmitted. The electrical signals carried by cables 66 are transmitted to a controller 68 (FIG. 5). The transmitted signals may be amplified by an amplifier (not shown) prior to being transmitted over cables 66, or they may be amplified by an amplifier adjacent to, or part of, controller 68, or they may not need to be amplified at all. Once controller 68 receives the electrical signals from cables 66, it processes them in a manner that will be described below in order to gather and determine various characteristics about a patient lying on support deck 28, such as the patient's heart rate, breathing rate, and/or whether the patient is experiencing a seizure or not.

The basic principle of various aspects of the present invention is that a person lying on a sleep surface positioned on support deck 28 will exert changing forces onto one or more of force sensors 44, and those changes can be monitored to determine useful information about the patient. For example, the beating of the patient's heart will exert small forces that are transferred to the support deck, and from the support deck to load frame 26 where they are detected by the force sensors 44. As another example, the patient's breathing creates forces that are transferred to the patient support deck 28 and load frame 26, where they are detected by force sensors 44. Still further, if a patient experiences a seizure, the movement of the patient's limbs and/or body will generate forces on support deck 28 that are transferred, via load frame 26, to force sensors 44. Force sensors 44 detect all of these various kinds of forces and convert them into electrical signals 70 (see, e.g. FIG. 6), which are then passed by cables 66 to controller 68 which performs an analysis of the data contained within the electrical signals 70.

Controller 68 may do several things with the electrical signals 70, one of which is the calculation of Fast Fourier Transforms. As is known in the art, the calculation of a Fourier Transform generates a spectrum illustrating the various frequency components of a time domain signal. As will be discussed below, the frequency spectrum generated by the Fast Fourier Transforms can be utilized by controller 68 in order to determine various characteristics about the patient. In addition to calculating the Fast Fourier Transforms of the electrical signals 70 from cables 66, controller 68 may also perform low-pass and band-pass filtering of signals 70. The low-pass filtering may be designed to remove those frequency components that are not needed for the analyses described herein. As will be discussed more below, the frequencies of interest for determining the patient's heart rate are primarily the second and third harmonics of the patient's heart rate. Thus, the low-pass filter should not, at a minimum, eliminate frequencies less than three times that of the maximum heart rate desired to be detected. The band-pass filtering may be used to remove the sixty hertz electrical noise from the electrical power supply.

Controller 68 may also combine the signals 70 from two or more of the force sensors 44 as part of the data analysis carried out by controller 68. The choice of which signals 70 to combine may be based upon changes in the center of gravity of the patient on support deck 28. The center of gravity of the patient may be determined by controller 68, or some other processing device, based upon the force signals generated by force sensors 44. One method by which controller 68, or another processing device, may determine the patient's center of gravity from force sensors 44 is disclosed in commonly-assigned U.S. Pat. No. 5,276,432, issued to Travis on Jan. 4, 1994, the complete disclosure of which is hereby incorporated herein by reference.

FIGS. 6-17 depict data that was generated from the measurements of a single force sensor 44 implemented as a load cell and positioned at the left, head end of a patient support apparatus. The patient support apparatus upon which these readings were taken was substantially similar to support apparatus 20. The various data depicted in these drawings correspond to different locations of a patient, as well as different time intervals for the various Fast Fourier Transforms illustrated therein, as will be discussed in greater detail below.

Figure 6:
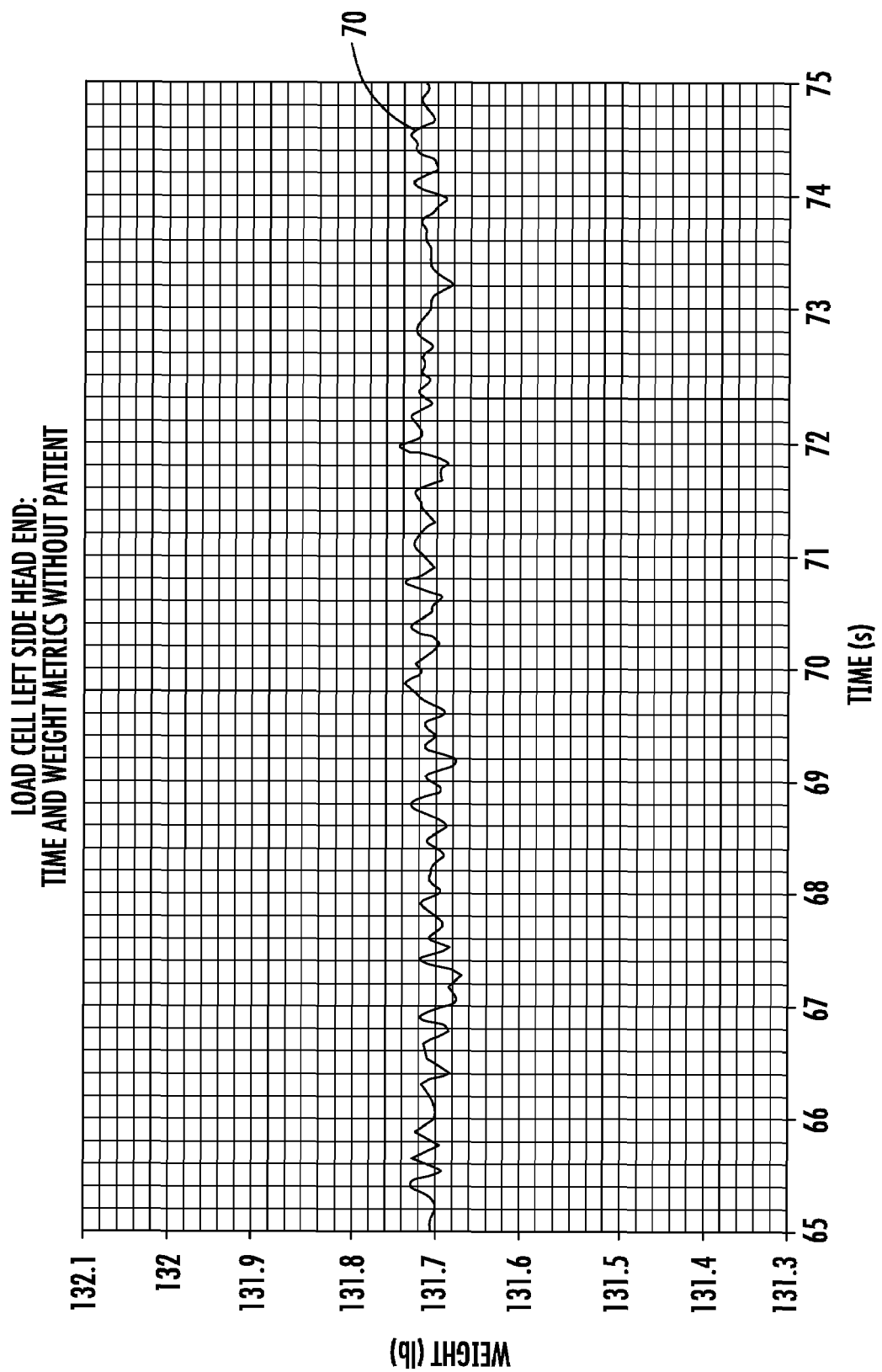
FIG. 6 is a graph of weight versus time generated by the measurements of one of the load cells taken when no person was supported on the patient support apparatus.

FIG. 6 depicts a graph of the signal 70 output from a single force sensor 44 taken when no patient was positioned on the support deck of the patient apparatus. As can be seen, the load cell measures a force of approximately 131.7 pounds, with very minor variations, over the course of a ten second time interval. This graph indicates the baseline fluctuation of the force sensor 44 when no patient is present.

Figure 7:
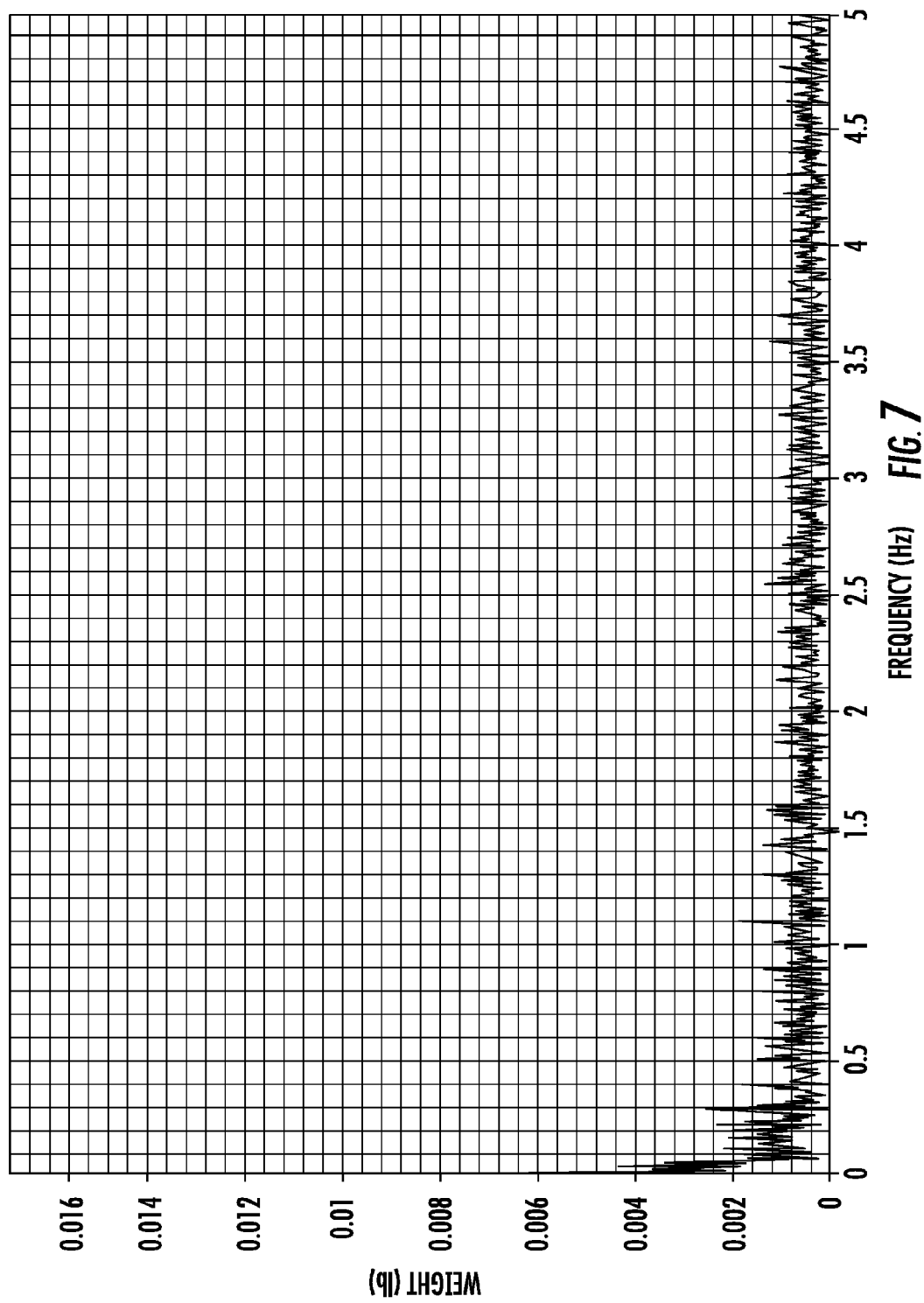
FIG. 7 is a graph of the Fast Fourier Transform of the graph of FIG. 6.

FIG. 7 depicts the Fast Fourier Transform of the graph of FIG. 6. FIG. 7 thus shows the frequency components of the graph of FIG. 6. As can be seen from FIG. 7, the frequency spectrum is almost uniformly close to zero for substantially all frequencies.

Figure 8:
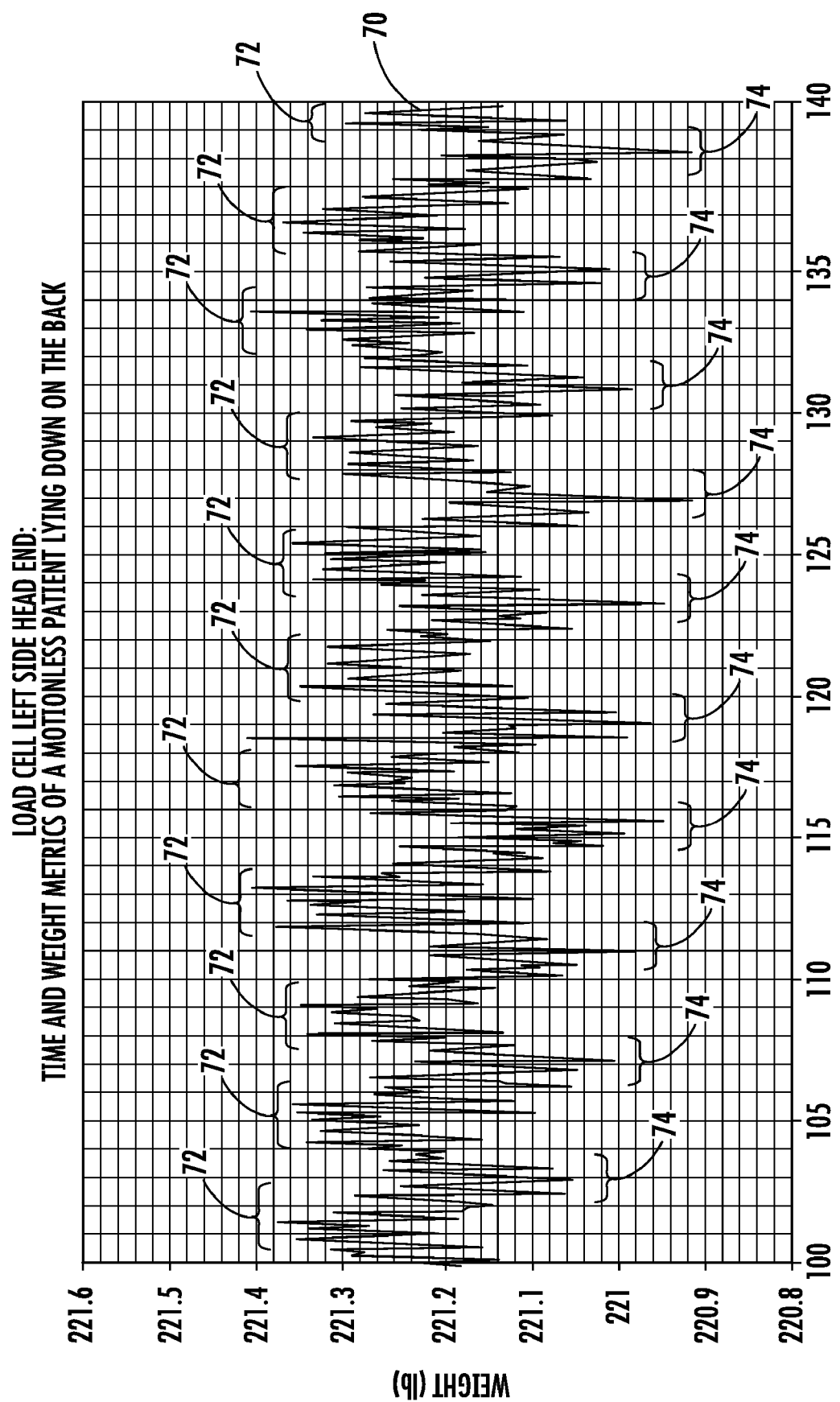
FIG. 8 is a graph of weight versus time generated by the measurements of one of the load cells taken when a person was lying substantially motionless on his back on the patient support apparatus.

FIG. 8 depicts the graph of the signal 70 output from a single force sensor 44 taken when a patient was lying down on his back on the support deck. As can be seen in FIG. 8, the signal 70 has eleven peaks 72 and ten valleys 74 over the forty second time interval depicted in FIG. 8. Peaks 72 and valleys 74 correspond to the breathing rate of a patient positioned on support deck 28. Controller 68 may be programmed to calculate a breathing rate from these peaks and valleys. In the graph of FIG. 8, the first peak 72 occurs at about 101 seconds, while the last valley 74 occurs at about 138.5 seconds. Thus, between 101 and 138.5 seconds, there are ten complete cycles illustrated in FIG. 8. This corresponds to a breathing rate of approximately 3.75 seconds per breath [(138.5−101)/10=3.75]. A breathing rate of 3.75 seconds per breath translates into a breathing rate of sixteen breaths per minute [(1/3.75)*60=16]. A person skilled in the art would be able to program controller 68, which may include one or more conventional microprocessors with suitable RAM and/or other memory, to analyze the time domain signal 70 of force sensor 44 in order to calculate a breathing rate of the patient.

Figure 9:
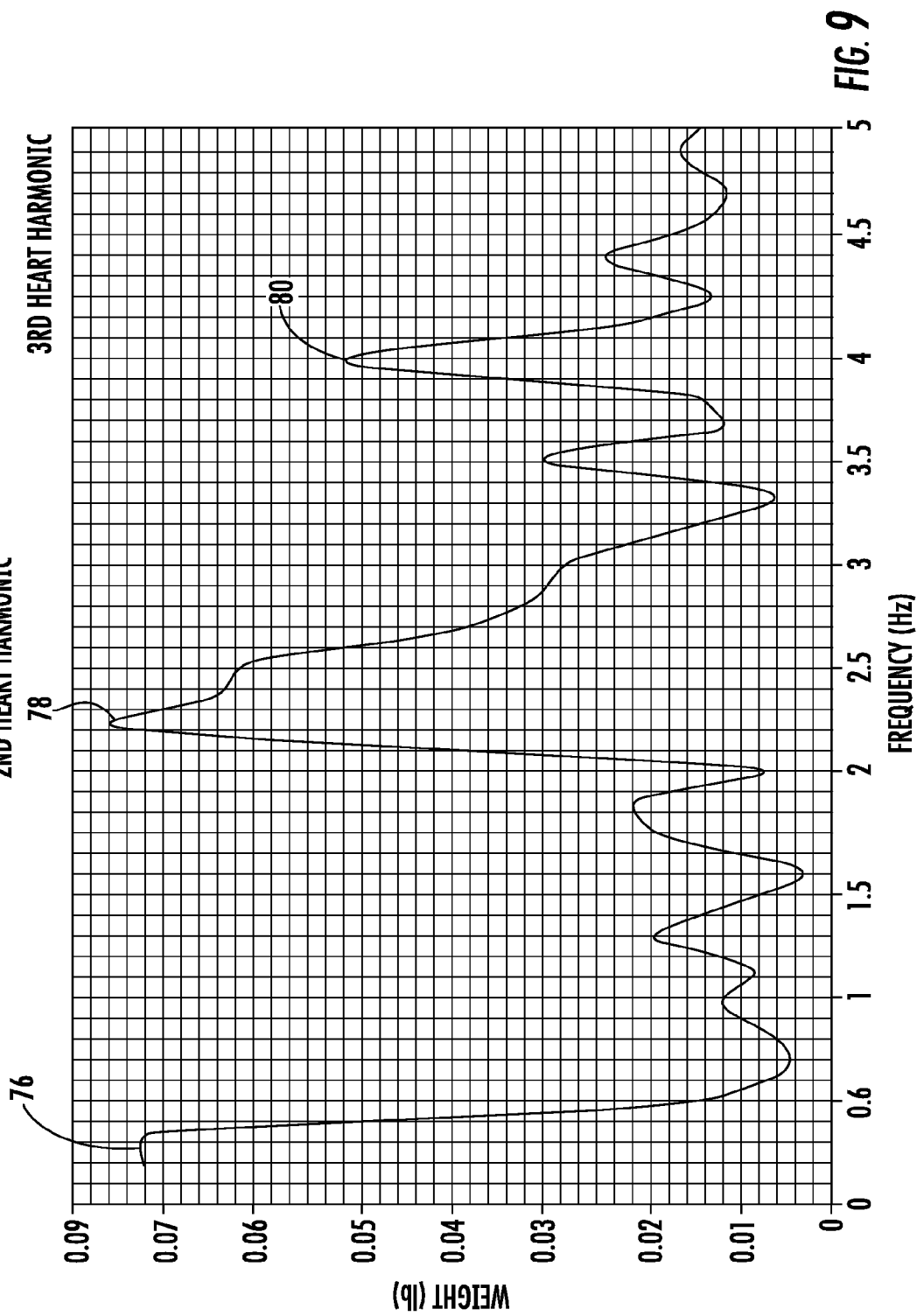
FIG. 9 is a graph of the Fast Fourier Transform of the graph of FIG. 8 taken over an interval of 6.35 seconds.

FIG. 9 illustrates a Fast Fourier Transform of the time domain signal 70 of FIG. 8 taken over a time interval of 6.35 seconds. Controller 68 may be programmed to carry out this Fast Fourier Transform, or another controller having one or more microprocessors and suitable memory, may be programmed to calculate this Fast Fourier Transform. As can be seen in FIG. 9, the chart has three major peaks. The leftmost peak 76 corresponds to a breathing rate of the patient. The second to leftmost peak 78 corresponds to a second harmonic of the patient's heart beat. The rightmost peak 80 corresponds to the third harmonic of the patient's heart beat.

Controller 68 may be programmed to automatically analyze the Fast Fourier Transforms of the signals 70 generated by force sensors 44, such as the Fast Fourier Transform depicted in FIG. 9. Such analysis may be used to determine the patient's heart rate and/or breathing rate. Using FIG. 9 as an example, the patient's breathing rate can be determined from the breathing rate peak 76. In FIG. 9, breathing rate peak 76 occurs at approximately 0.28 hertz. This corresponds to a breathing rate of about 16.8 breathes per minute [60*0.28=16.8]. This matches closely with the breathing rate of 16 breathes per minute that was calculated above using the time domain signal 70 of FIG. 8. (The discrepancy can be accounted for due to the different time periods over which the breathing rate was measured: the FIG. 8 calculation used a time period of 37.5 seconds while the FIG. 9 calculation used a time period of 6.35 seconds).

In addition to determining a patient's breathing rate, controller 68 may further be programmed to determine the patient's heart rate using the Fast Fourier Transform of signal 70. This can be accomplished by looking at the peaks 78 and 80, which, as noted, correspond to the second and third harmonics of the patient's heart beat, respectively. Using FIG. 9 as an example, peak 78 occurs approximately at 2.2 hertz and peak 80 occurs approximately at 3.9 hertz. Since these peaks represent the second and third harmonics of the patient's heart beat, the first harmonic can be easily calculated by either dividing the second harmonic frequency by two, or dividing the third harmonic frequency by three. If the results of these two different computations differ, it may be beneficial to compute an average of the two.

In the example of FIG. 9, the patient's heart rate can be calculated by dividing the frequency at peak 78 (approximately 2.2 hertz) by two to obtain a value of 1.1 hertz. Alternatively, the patient's heart rate can be calculated by dividing the frequency at peak 80 (approximately 3.9) by three to obtain a value of 1.3 hertz. Because this value differs from the 1.1 hertz value calculated using peak 78, the two values can be averaged together. Such an averaging would yield a heart rate of 1.2 hertz [(1.3+1.1)/2=1.2], which translates into a heart rate of 72 beats per minute.

Figure 10:
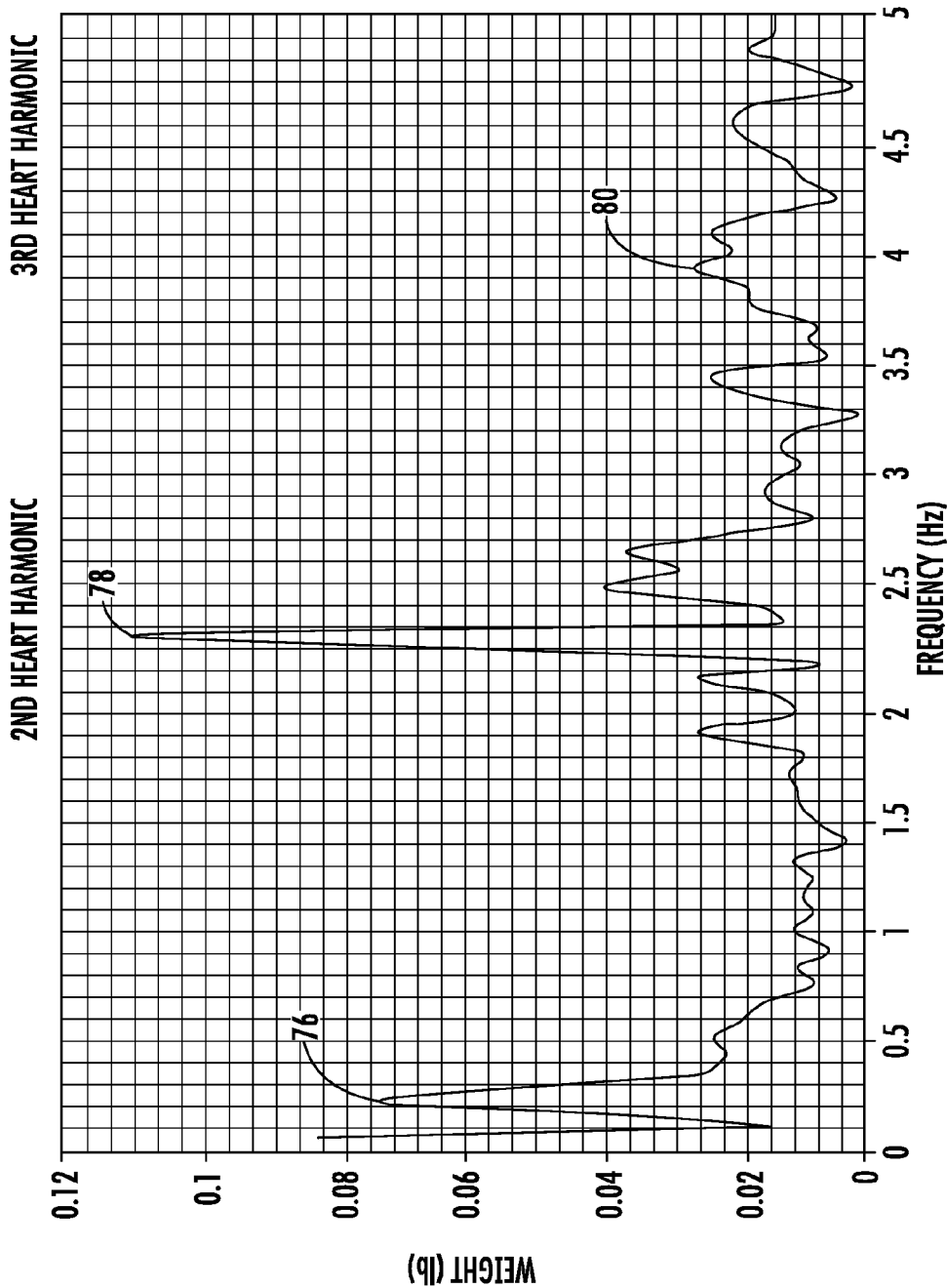
FIG. 10 is a graph of the Fast Fourier Transform of the graph of FIG. 8 taken over an interval of 12.75 seconds.

FIG. 10 illustrates a Fast Fourier Transform of the signal 70 of FIG. 7 taken over a time interval of 12.75 seconds, which is greater than the time interval of FIG. 8. While this graph shows that the peak 80 of the third harmonic has been diminished, it is still possible for controller 68 to calculate both the patient's heart rate and breathing rate from this graph. The breathing rate is defined by peak 76 which, in FIG. 8, is located at approximately 0.24 hertz, corresponding to a breathing rate of about 14.4 breathes per minute. The heart rate can be determined by dividing the frequency of the second harmonic peak 78 by two. In FIG. 10 this yields a heart rate of approximately 1.125 hertz [2.25/2=1.125], or 67.5 beats per minute. Alternatively, the heart rate can be calculated using the frequency at the third harmonic peak 80, which occurs approximately at 3.9 hertz. Dividing this frequency by three, yields a heart rate of 1.3 hertz, which can either be used alone as the heart rate, or can be combined with the heart rate generated from the frequency of second peak 78. The combination of the two heart rates can be done by averaging, or by any other suitable mathematical technique.

Figure 11:
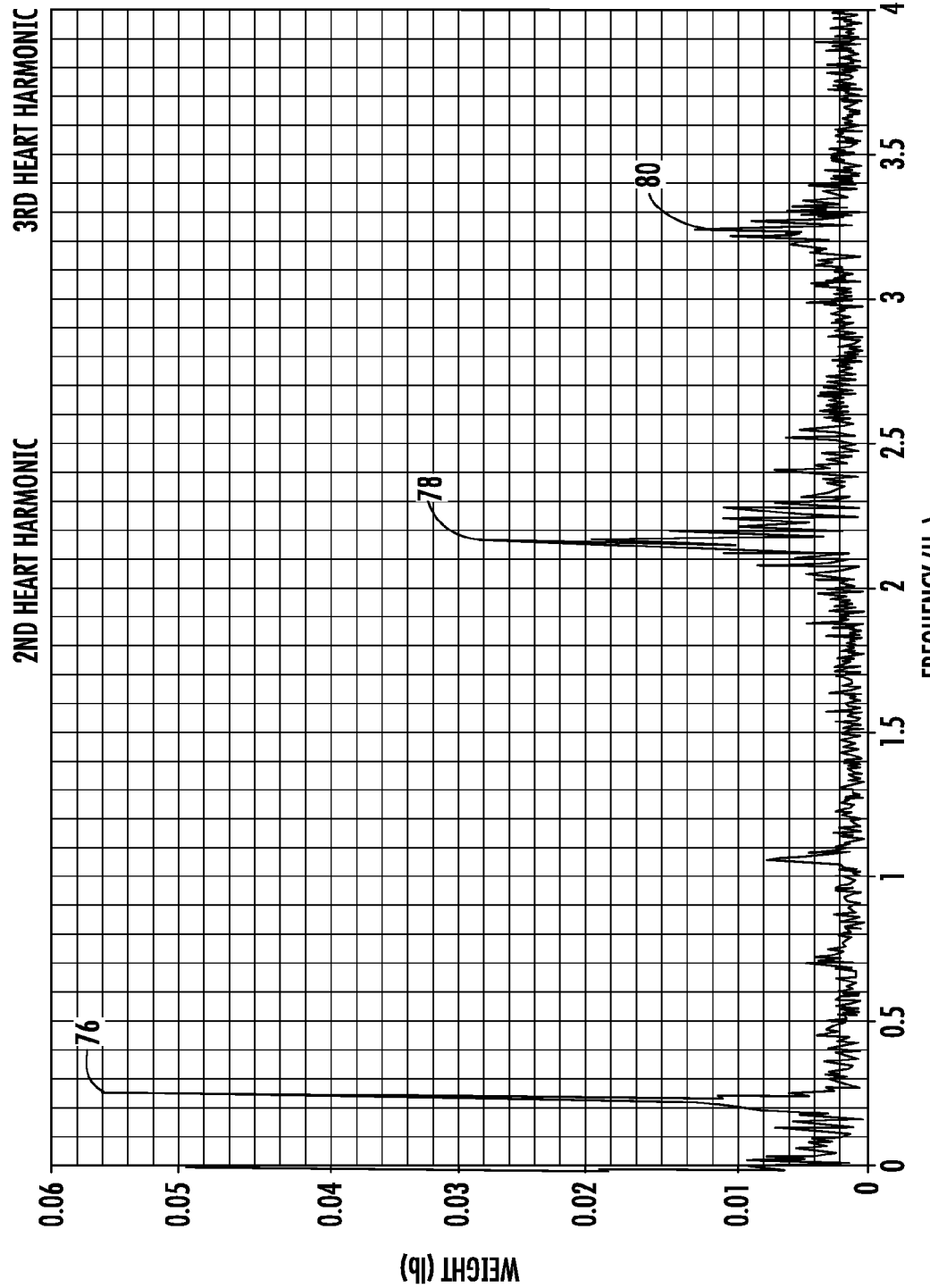
FIG. 11 is a graph of the Fast Fourier Transform of the graph of FIG. 8 taken over an interval of 204.8 seconds.

FIG. 11 illustrates another Fast Fourier Transform of the time domain signal 70 of FIG. 8 taken over a time interval of 204.8 seconds. As can be seen, peaks 76, 78, and 80 are clearly defined and the breathing rate and/or heart rate of a patient can be determined from these peaks using any of the methods described above. While the peaks of FIG. 11 are clearly defined, this clarity comes at a cost of a relatively lengthy time interval of 204.8 seconds. In some situations, this "cost" may be perfectly acceptable, and in other situations, this "cost" may desirably be avoided. In general, the longer the time period used for the Fast Fourier Transform, the clearer the peaks. However, in general, the longer the time period used in the Fast Fourier Transforms, the less often one can determine the heart rate and/or breathing rate. Thus, longer time intervals can be useful for accurately determining relatively steady heart rates and/or breathing rates, while longer time intervals may be less effective for determining short term trends and/or changes. A person skilled in the art would be able to choose the most suitable time interval for a given situation, and the present invention contemplates, in addition to using a single time interval, using time intervals of different durations at different times, as well as using different time intervals for two or more of the force sensors 44.

Figure 12:
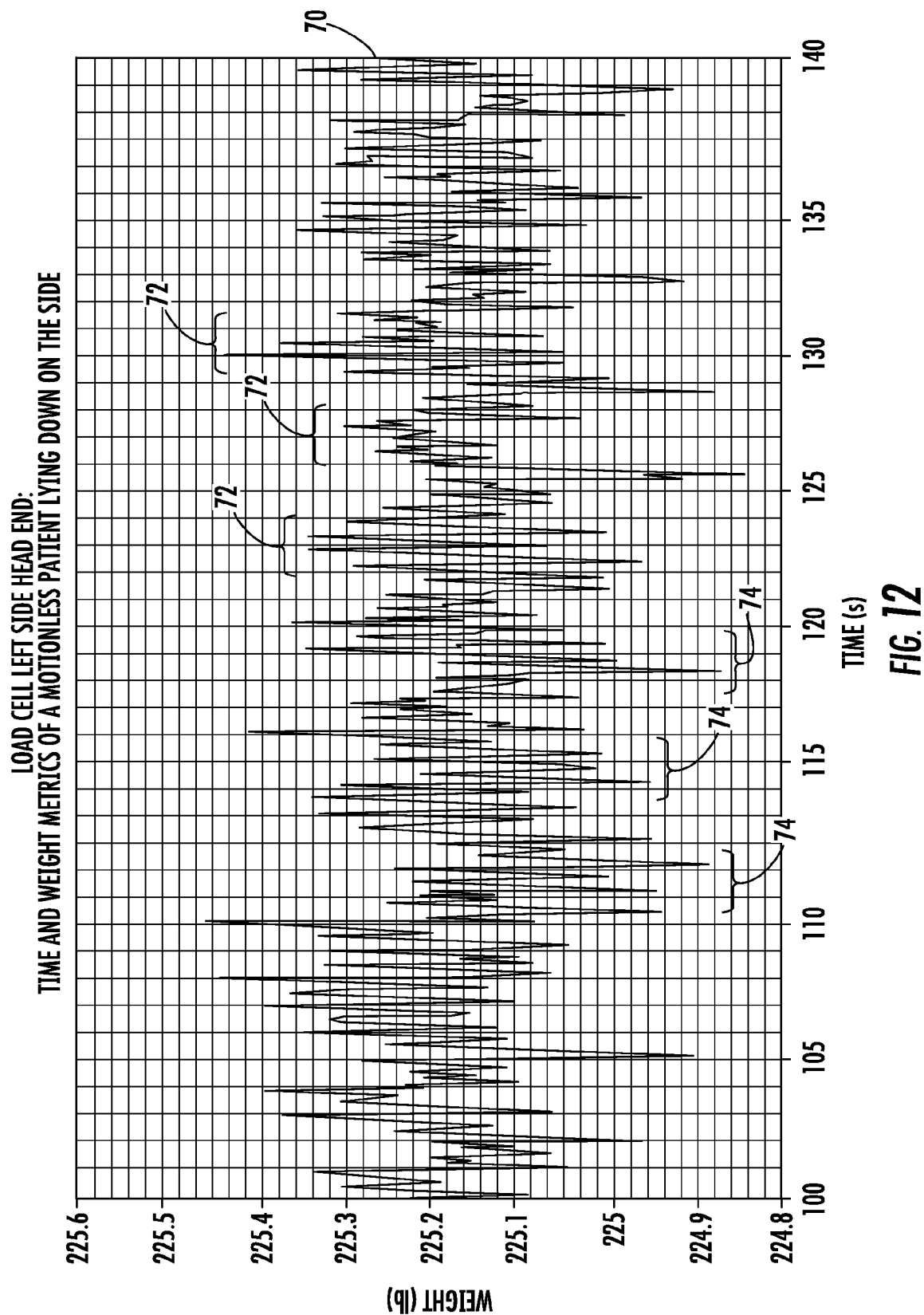
FIG. 12 is a graph of weight versus time generated by the measurements of one of the load cells taken when a person was lying substantially motionless on his side on the patient support apparatus.

FIG. 12 illustrates a time domain signal 70 generated by a force sensor 44 while a patient was lying on his side on top of the support deck of a patient support apparatus. The peaks 72 and valleys 74 corresponding to the patient's breathing rate are evident, and controller 68 could be programmed to determine the patient's breathing rate directly from time domain signal 70. Alternatively or additionally, controller 68 could be programmed to determine the patient's breathing rate using a Fast Fourier Transform of the time domain signal.

Figure 13:
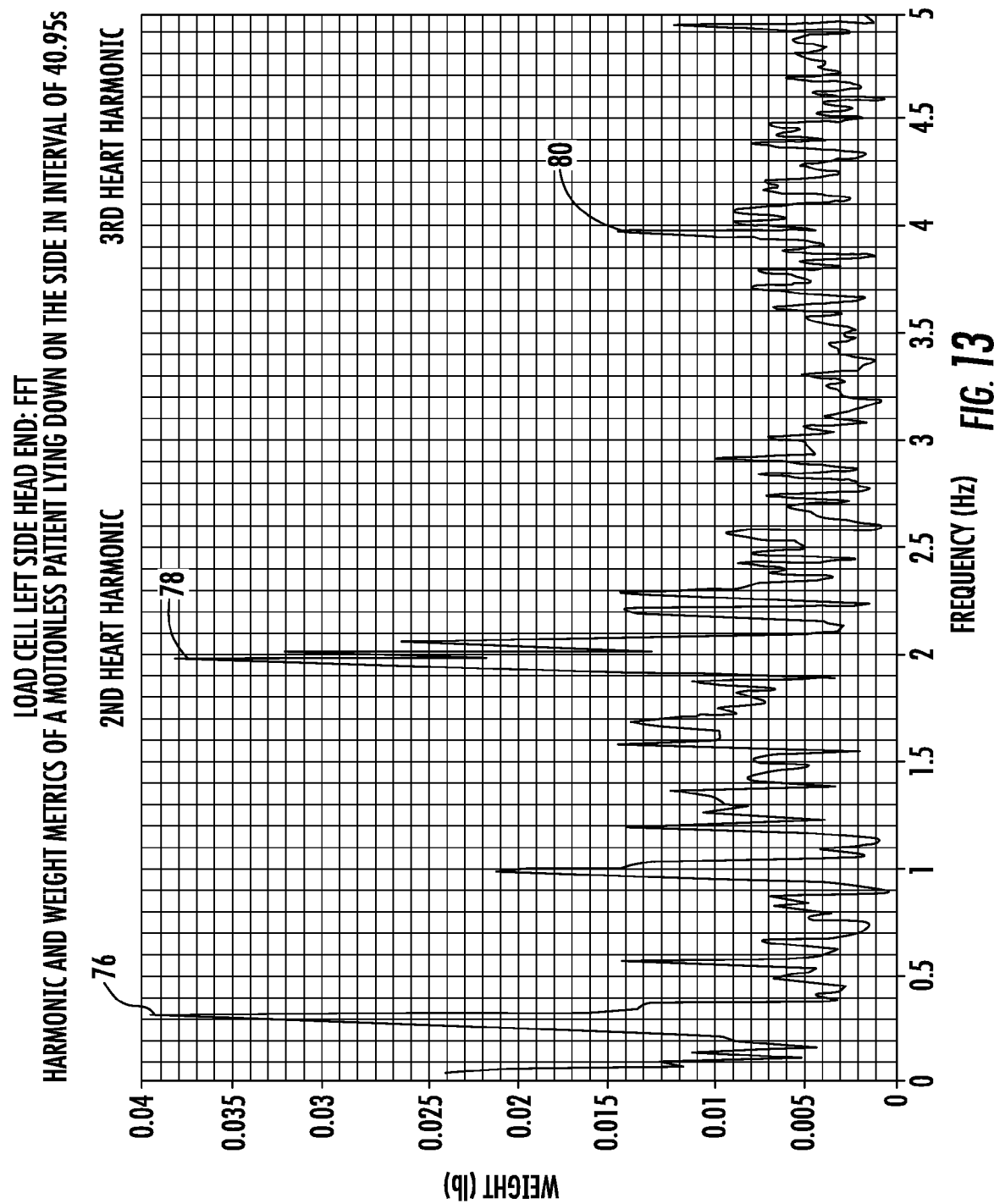
FIG. 13 is a graph of the Fast Fourier Transform of the graph of FIG. 12 taken over an interval of 40.95 seconds.

FIG. 13 illustrates a Fast Fourier Transform of the time domain signal 70 of FIG. 12 taken over a time interval of 40.95 seconds. Peaks 76, 78, and 80 are clearly visible and can be used to determine heart rate and/or breathing rate in the manner described above.

Figure 14:
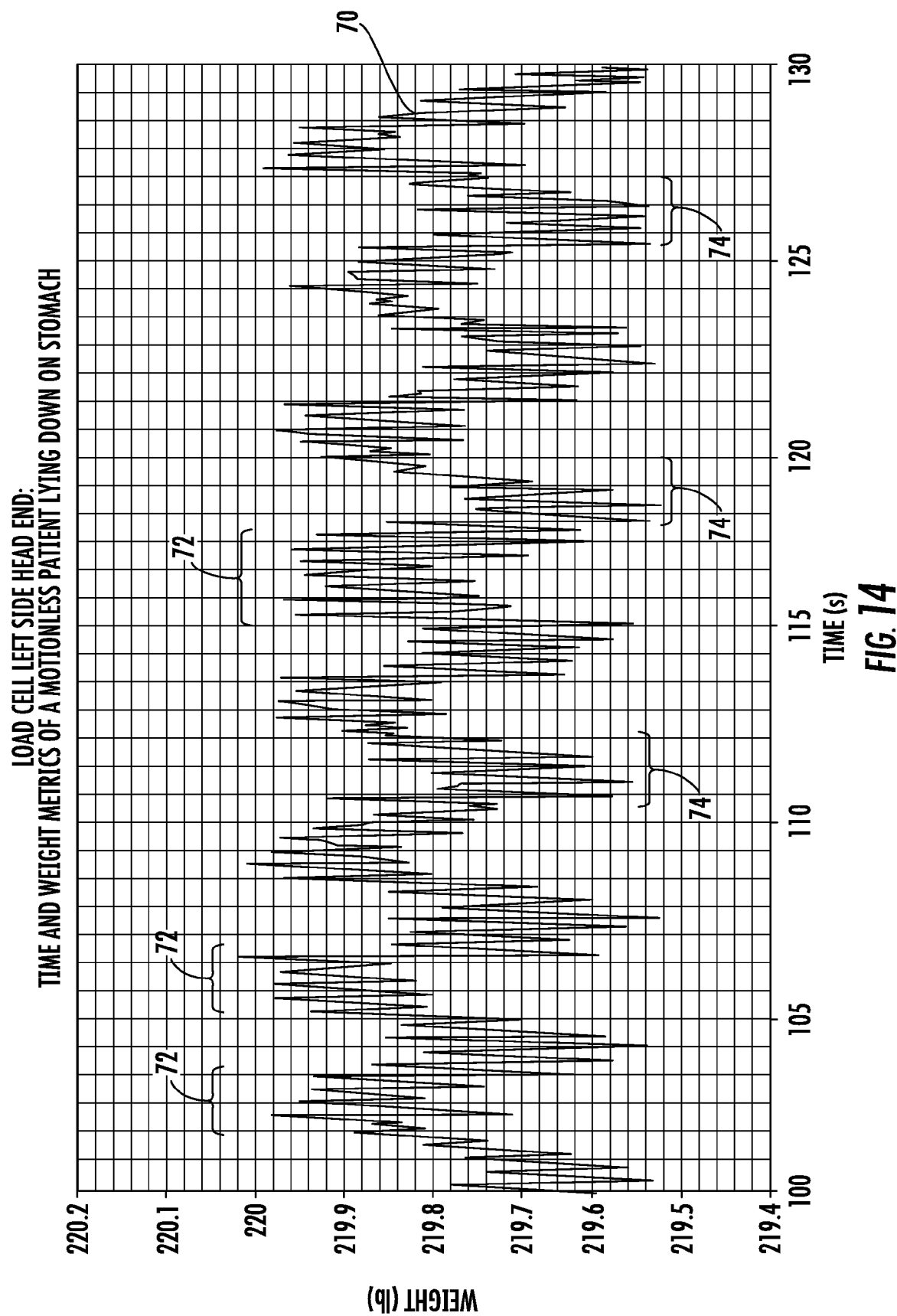
FIG. 14 is a graph of weight versus time generated by the measurements of one of the load cells taken when a person was lying substantially motionless on his stomach on the patient support apparatus.

FIG. 14 illustrates a time domain signal 70 generated by a force sensor 44 while a patient was lying on his stomach on top of the support deck of a patient support apparatus. The peaks 72 and valleys 74 are evident, and controller 68 could determine a patient's breathing rate directly from the time domain signal 70 of FIG. 14.

Figure 15:
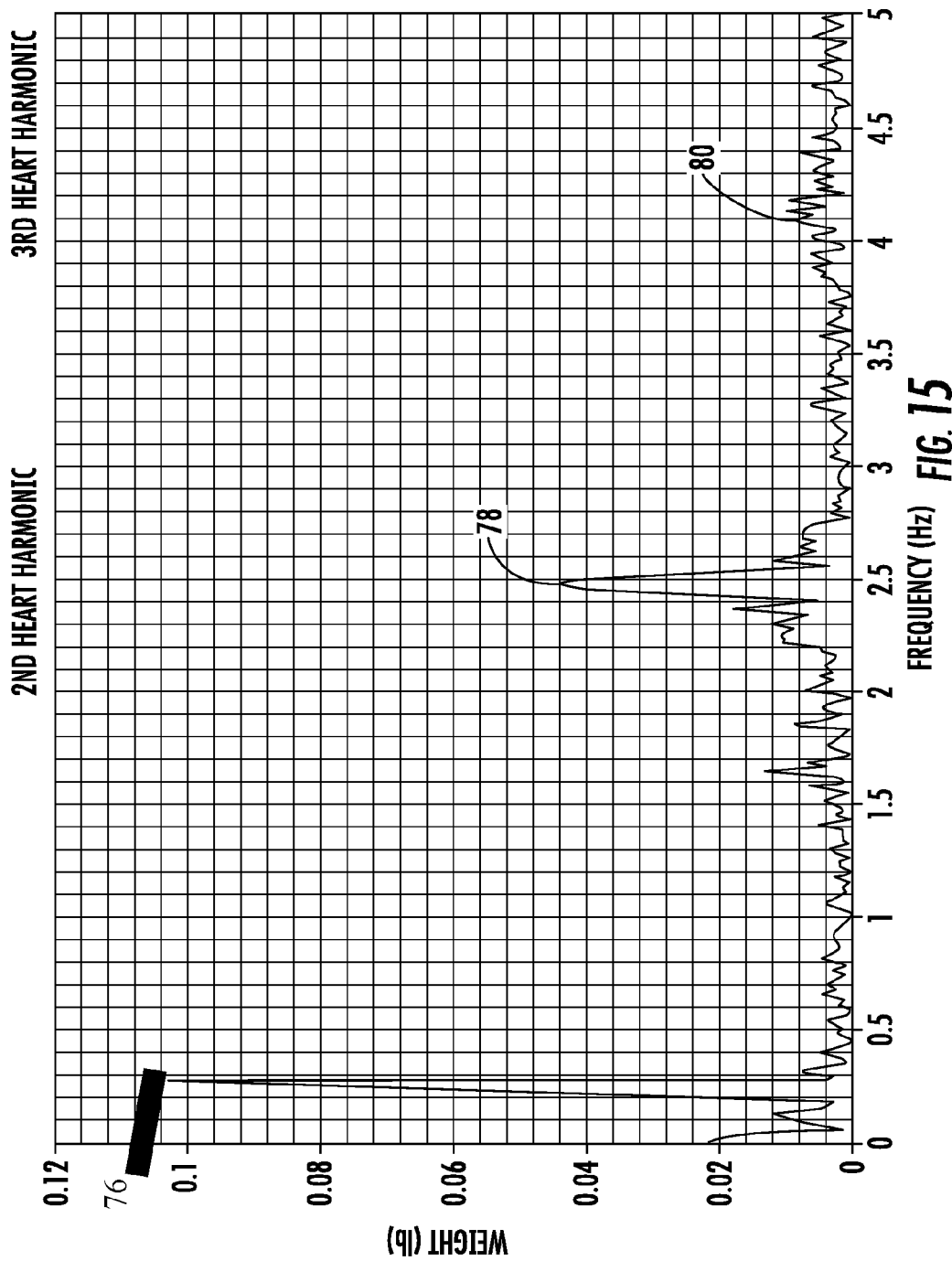
FIG. 15 is a graph of the Fast Fourier Transform of the graph of FIG. 14 taken over an interval of 40.95 seconds.

FIG. 15 illustrates a Fast Fourier Transform of the time domain signal 70 of FIG. 14 taken over a time interval of 40.95 seconds. Peaks 76 and 78 are clearly visible, and these are sufficient for controller 68 to determine either or both of the patient's heart rate and breathing rate in the manner described above.

Figure 16:
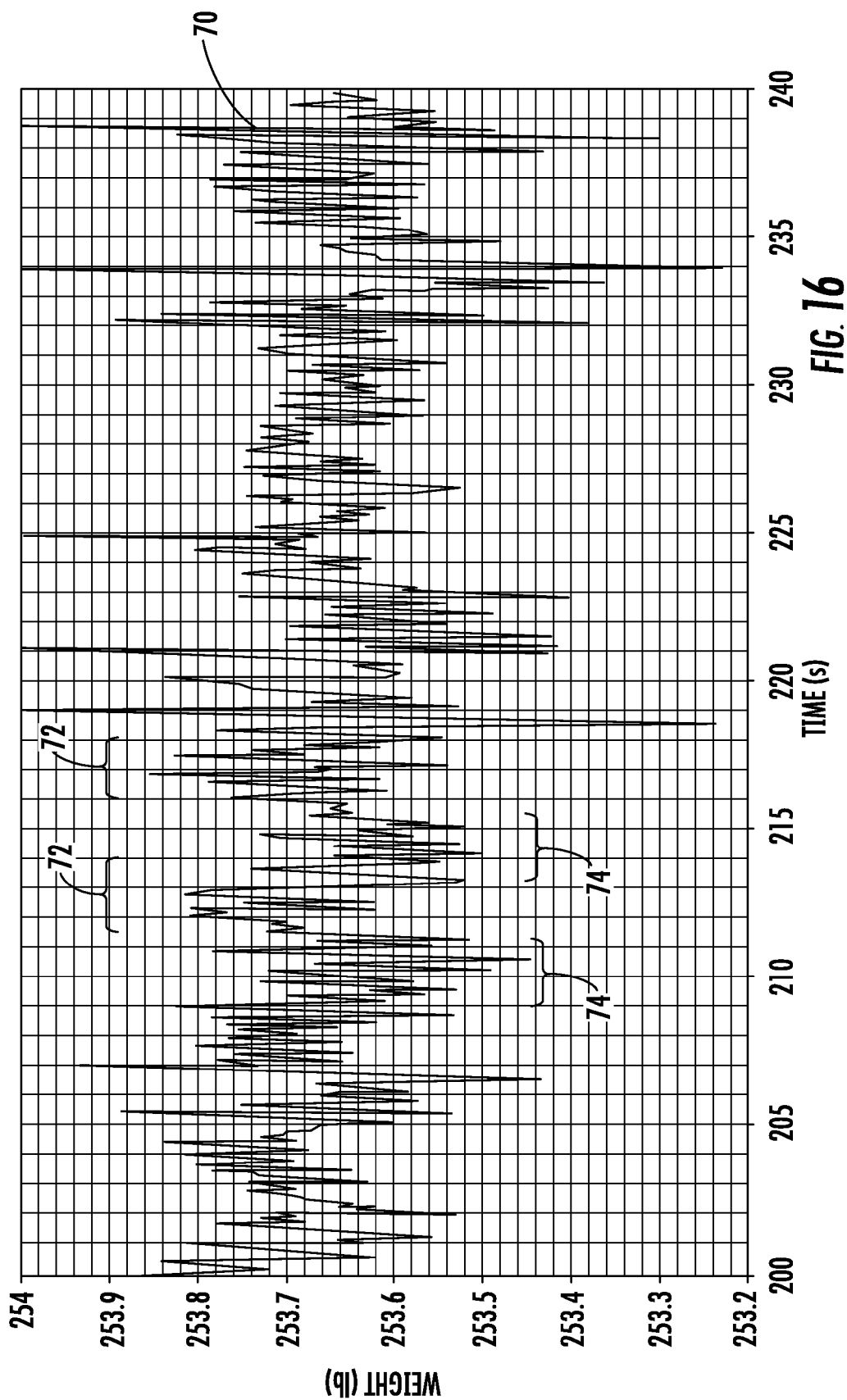
FIG. 16 is a graph of weight versus time generated by the measurements of one of the load cells taken when a person was in the sitting-up position on the patient support apparatus.
Figure 17:
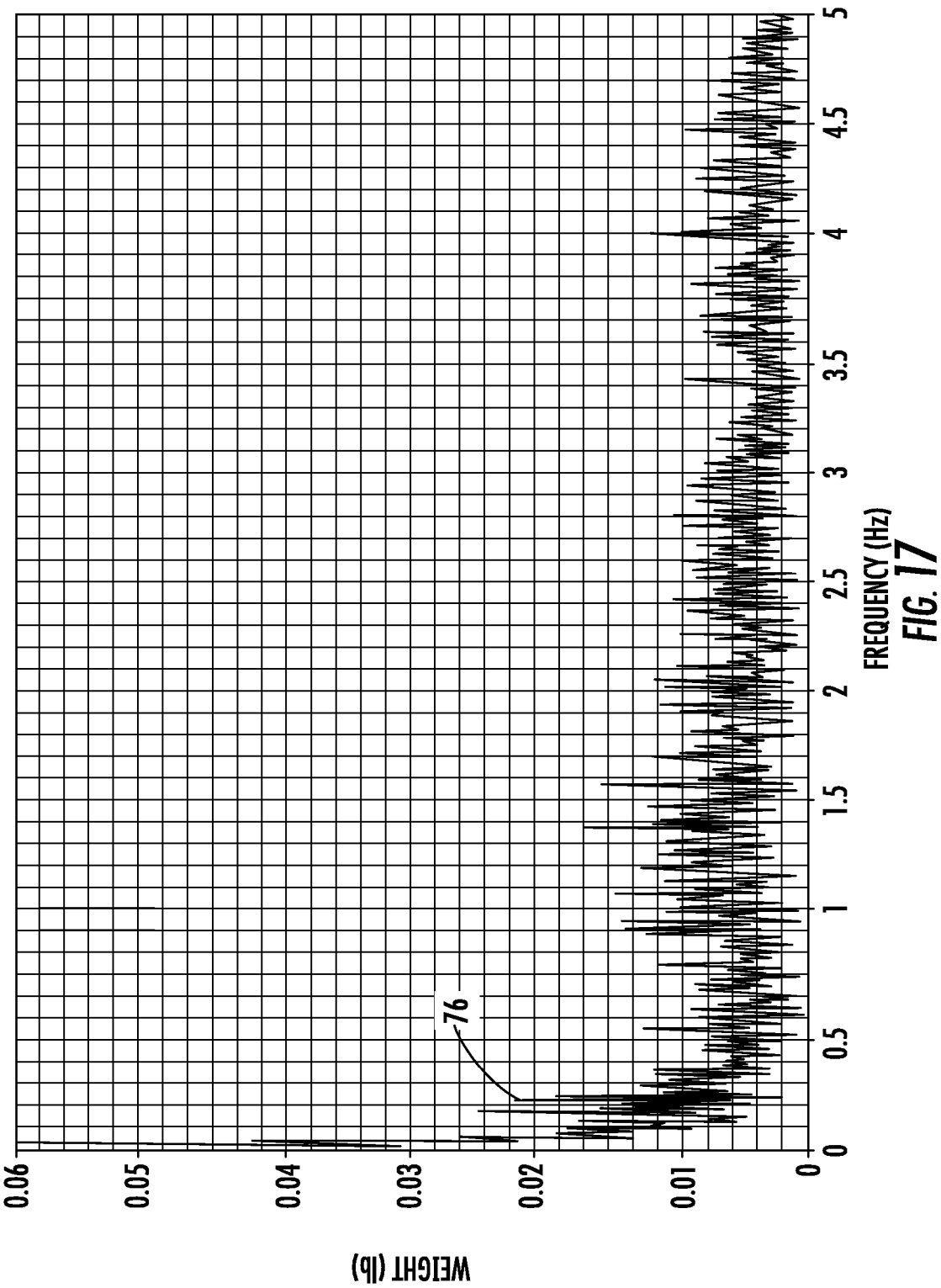
FIG. 17 is a graph of the Fast Fourier Transform of the graph of FIG. 16 taken over an interval of 40.95 seconds.

FIG. 16 illustrates a time domain signal 70 generated by a force sensor 44 while a patient was sitting up on top of the support deck of a patient support apparatus. This data was generated when the person's torso was not in contact with the head section 36 of the patient support deck. Thus, the vibrations of the patient's heart beat were likely muted by the patient's body, thereby explaining the lack of clear second and third harmonic heart beat peaks 78 and 80 (FIG. 17). FIG. 18, however, does show a breathing rate peak 76, and FIG. 17 also shows peaks and valleys 72 and 74. Consequently, a patient's breathing rate could be calculated either from the direct time domain signal 70 or a Fast Fourier Transform of those signals.

The charts of FIGS. 6-17 demonstrate the viability of using one or more force sensors 44 to determine and monitor one or more of a patient's conditions. While FIG. 17 suggests that it may be difficult to determine a patient's heart rate while the person is sitting up on the patient support apparatus, additional signal processing could be done to mitigate this difficulty. The charts of FIGS. 6-17 thus confirm the usefulness of monitoring the fluctuations of force sensors to determine one or more characteristics about a patient positioned on a support apparatus, such as patient support apparatus 20.

In addition to monitoring the breathing rate and/or heart rate of a patient, controller 68 can also be configured to determine if a patient is experiencing a seizure or not. In order to detect seizures, controller 68 monitors the amplitude of signals 70 for repetitive fluctuations that exceed a predetermined magnitude over a predetermined time period. Such monitoring may be done on signals that are not filtered, or that are filtered in a different manner than is done to the signals used to monitor the patient's heart rate and/or breathing rate. The predetermined magnitude and predetermined time that the fluctuations of signal 70 has to exceed in order to qualify as a seizure may be adjustably set by a health care attendant so as to be able to be specifically tailored to a particular patient. Alternatively, the predetermined magnitude of the changes from one or more force sensors 44 may be based upon a percentage of the patient's resting weight such that a lighter patient won't have to cause as great of amplitude variations in signal 70 as a heavier person would before controller 68 determined a seizure was occurring. Because the movements of a patient experiencing a seizure generally occur at random, it is not necessary to calculate a Fast Fourier Transform of the signals 70 in order to detect a seizure.

Controller 68 may further be configured so as to issue one or more alerts or alarms if one or more of a variety of conditions occur. Controller 68 may be programmed to issue an alert or alarm if either of the breathing rate and/or pulse rate rises above, or drops below, predetermined levels. The predetermined levels may be adjustable by a health care attendant either through a control panel (not shown) on patient support apparatus 20 having a user interface that allows the attendant to input desired levels, or through a connection to a remote computer, or computer network, to which patient support apparatus 20 may be in electronic communication. Additionally or alternatively, controller 68 may be configured to issue an alert if either of the breathing rate or heart rate experiences a change that exceeds a specified amount over a specified time period, wherein the specified amount and specified time period may be set by health care attendants. Further, controller 68 may desirably be configured to issue an alert if forces are detected on one or more force sensors 44 that are indicative of a potential seizure. Controller 68 may also issue an alert if it is unable to detect a heart rate and/or a breathing rate. The particular alert or alarm issued by controller 68 can take on any form that is suitable for a given environment, and may include visual and/or audio indications generated by patient support apparatus 20, or it may include the transmission of an alert or alarm signal to a remote location, such as a hospital computer network, that then processes the signal in the correct manner, such as by forwarding it to a nurse's station.

Controller 68 may determine heart rate, breathing rate, and seizure status of a patient based upon the output of only a single force sensor 44, or it may make one or more of those determinations based upon the output (i.e. signals 70) of more than one force sensor 44. In the cases where more than one force sensor 44 is used to determine heart rate, breathing rate, and/or patient seizure status, the processing of signals 70 from each force sensor 44 can be accomplished through any suitable combinations of the signals, such as by processing each signal individually and then combining the results in an appropriate manner (such as averaging), or by combining one or more of the signals prior to processing, or at some point prior to the final processing of the signals.

Still further, the particular manner in which controller 68 processes the signals may vary depending upon other circumstances or conditions of patient support apparatus 20. For example, if controller 68 is adapted to determine the patient's center of gravity, controller 68 could be configured to assign a greater weight to the signals 70 coming from the force sensor 44 closest to the center of gravity. Alternatively, controller 68 may assign a greater weight to the two closest force sensors 44 to the center of gravity. Additionally, controller 68 may be in communication with one or more angle sensors that determine the angle of one or more of the sections 36, 38, and 40 of support deck 28. This angular information could be used to alter the processing of the signals 70. Still other circumstances or conditions of patient support apparatus 20 can be taken into account when processing the signals 70, if desired.

In addition to, or in lieu of, the Fast Fourier Transform calculations made by controller 68 on the signals 70 coming from one or more force sensors 44, controller 68 may perform other processing beyond that described above to usefully enhance the data generated by force sensors 44. One such type of processing may involve digital signal processing that does not utilize any Fast Fourier Transforms at all. Another such possible processing may involve the computation of one or more Fast Fourier Transforms of a previously computed Fast Fourier Transform. Such a multiple calculation of Fourier Transforms is know as a cepstrum, and may provide additional data that can be used to refine or assist in the determination of the patient's heart rate and/or breathing rate. Controller 68 may also perform processing to separate or minimize the impact of normal patient movement upon the calculations of heart rate, breathing rate, and/or seizure detection. Such processing may take into account changes in the location of the patient's center of gravity, the angular orientation of support deck sections 36, 38, 40 and 42, or still other factors.

Controller 68 may also store the data of signals 70 and/or the Fast Fourier Transforms in a memory (not shown) which can be read for displaying to attendant personnel so that they can look at and manually analyze the raw data. The memory may be located on patient support apparatus 20, or it may be located at a location remote from patient support apparatus, or both. If located remotely, controller 68 may communicate the data by any known means, such as a wire or cable connection, or via any of a variety of different conventional wireless communication techniques. Controller 68 may also be located remotely from patient support apparatus 20 and receive signals 70 via a wired or wireless connection to patient support apparatus 20.

Because of the computational resources necessary for calculating Fast Fourier Transforms, and/or performing other computationally heavy digital signal processing, controller 68 may include one or more processors specifically dedicated to the functions of monitoring the force sensors 44. Alternatively, the one or more processors of controller 68 may perform other patient support apparatus functions besides the monitoring of forces sensors 44, such as the control of various motors, the monitoring of other medical equipment and/or patient support apparatus sensors, and other tasks. Still further, controller 68 may have some components physically located on patient support apparatus 20 and some components located remotely that communicate in any suitable manner with each other. However controller 68 is implemented, it is configured to carry out one or more of the functions described herein.

In addition to determining a patient's heart rate, breathing rate, and/or seizure status, controller 68 can also be configured to determine a patient's weight from force sensors 44. Such a determination of weight can be carried out in a known manner by analyzing the signals 70 from the various force sensors 44. The monitoring of the patient's weight may also be performed as part of, or separately from, a patient bed exit system in which controller 68 issues an alert when it detects that the patient's weight has substantially or completely been lifted off of patient support deck 28. Such a lifting of the patient's weight indicates the patient has left, or is about to leave, patient support apparatus 20, and such information may desirably be communicated to remote locations.

The system of one or more force sensors 44 and controller 68 can be implemented on any patient support apparatus, not just the patient support apparatus 20 illustrated and described herein. Any patient support apparatus, such as a bed, cot, stretcher, or the like, in which one or more force sensors can be placed and their outputs analyzed can be adapted to include the monitoring system of the present invention. Such force sensors may be placed in any location where they are capable of detecting force changes caused by the breathing and heart beating of the patient.

While the systems and methods discussed herein have been previously described with reference to calculations of Fast Fourier Transforms, it will be understood by those skilled in the art that other mathematical techniques besides Fast Fourier Transforms can be used to carry out the systems and methods of the present invention.

Another embodiment of the present invention includes a method for analyzing forces exerted by a patient on a patient support, such as patient support apparatus 20, or any other patient support. The method includes the simultaneous monitoring of one or more patient conditions of interest (e.g. heart rate, breathing rate, seizure status, or others) via two sensors, or two sets of sensors. The first sensor or sensor set is a sensor specifically adapted to measure the condition of interest (such as a sleeve that directly measures a patient's heart rate, for example). The second sensor or sensor set is the one or more force sensors 44. After readings from the force sensors 44 are taken over a suitable time period, those readings are compared with the measurements from the first sensor (or first sensor set). The comparison involves looking for correlations between the readings from the first sensor (or first sensor set) and the second sensor (or second sensor set). After such a correlation is determined, the second sensor (or second sensor set) can thereafter be used to determine the condition of interest without the first sensor (or first sensor set) by examining the data from the second sensor (or sensor set) and using the known correlation between that data and the outputs of the first sensor (or sensor set). This method is a generalized method that allows correlations between force sensors 44 and various patient conditions to be discovered and refined, such as the patient heart rate, breathing rate, and seizure status, as well as other patient conditions.

While the present invention has been described herein in terms of several embodiments, it will be understood by those skilled in the art that the present invention is not limited to these particular embodiments, but includes any and all modification that are within the scope and spirit of the invention as defined in the following claims.

What is claimed is:

1. A patient support apparatus comprising:
   a support deck adapted to support a patient, said support deck including a plurality of sections pivotable with respect to each other such that a position of a patient's body supported on said support deck may be changed;
   a load frame supporting said support deck;
   a force sensor adapted to detect a force exerted from said load frame onto said force sensor, said force sensor outputting a signal corresponding to said force; and
   a controller in communication with said force sensor, said controller adapted to determine from said signal both a breathing rate and heart rate of a patient positioned on said support deck.

2. The apparatus of claim 1 wherein said controller is adapted to calculate a Fast Fourier Transform of said signal and use said Fast Fourier Transform to determine at least one of the breathing rate and the heart rate.

3. The apparatus of claim 2 wherein said controller identifies a peak frequency in said Fast Fourier Transform in order to determine the breathing rate.

4. The apparatus of claim 3 wherein the controller determines the breathing rate to be equal to said peak frequency.

5. The apparatus of claim 2 wherein said controller analyzes a harmonic peak in said Fast Fourier Transform in order to determine the heart rate.

6. The apparatus of claim 5 wherein said controller calculates the heart rate by dividing said harmonic peak by an integer greater than one that corresponds to said harmonic peak.

7. The apparatus of claim 5 wherein said controller analyzes a pair of peaks in said Fast Fourier Transform to determine the heart rate, said pair of peaks located at integer multiples of the heart rate.

8. The apparatus of claim 1 further including a low pass filter adapted to filter out frequencies in said signal that exceed a selected frequency.

9. The apparatus of claim 1 wherein said controller is further adapted to analyze said signal to determine if the patient is experiencing a seizure.

10. The apparatus of claim 2 further including a second force sensor adapted to detect a second force exerted from said load frame onto said second force sensor, said second force sensor outputting a second signal corresponding to said second force;
    wherein said controller is in communication with said second force sensor and said controller is further adapted to make a second determination of the breathing rate and the heart rate of the patient positioned on said support deck based upon said second signal.

11. The apparatus of claim 1 wherein said controller is further adapted to monitor the breathing rate and the heart rate and issue a notification to an attendant if either of the breathing rate and the heart rate meets a criteria.

12. A patient support apparatus comprising:
    a support deck adapted to support a patient, said support deck including a plurality of sections pivotable with respect to each other such that a position of a patient's body supported on said support deck may be changed;
    a load frame adapted to support said support deck, said load frame remaining generally stationary and flat as sections of said support deck are pivoted with respect to each other;
    an intermediate frame adapted to support said load frame;
    a force sensor interconnected between said load frame and said intermediate frame, said force sensor adapted to detect a force exerted from said load frame onto said force sensor, said force sensor outputting a signal corresponding to said force; and
    a controller in communication with said force sensor, said controller adapted to determine from said signal a breathing rate of a patient positioned on said support deck.

13. The apparatus of claim 12 wherein said controller is adapted to calculate a Fast Fourier Transform of said signal and use said Fast Fourier Transform to determine the breathing rate.

14. The apparatus of claim 12 wherein said controller is further adapted to monitor said breathing rate and issue a notification to an attendant if the breathing rate meets a criteria.

15. The apparatus of claim 14 wherein said controller allows said criteria to be changed by the attendant.

16. The apparatus of claim 14 wherein said controller is in communication with at least one computer located outside of a room in which the patient support apparatus is located.

17. The apparatus of claim 16 wherein said controller is further adapted to determine a heart rate of the patient using said Fast Fourier Transform.

18. The apparatus of claim 12 wherein said controller is further adapted to use said signal to determine whether the patient is having a seizure or not.

19. A patient support apparatus comprising:
    a support deck adapted to support a patient, said support deck including a plurality of sections pivotable with respect to each other such that a position of a patient's body supported on said support deck may be changed;
    a load frame supporting said support deck;
    a force sensor in contact with said load frame, said force sensor adapted to detect a force exerted from said load frame onto said force sensor, said force sensor outputting a signal corresponding to said force; and
    a controller in communication with said force sensor, said controller adapted to analyze said signal to determine if a patient positioned on said support deck is experiencing a seizure or not.

20. The apparatus of claim 19 wherein said controller is further adapted to calculate a Fast Fourier Transform of said signal and to determine from said Fast Fourier Transform a breathing rate of the patient.

21. The apparatus of claim 20 wherein said controller is further adapted to determine from said Fast Fourier Transform a heart rate of the patient.

22. A method of collecting data about a patient comprising:
    providing a support that supports at least a portion of a patient's weight;
    providing a force sensor that senses a force exerted by said support on said force sensor, said force sensor generating a signal corresponding to said force;
    providing a controller in communication with said force sensor;
    performing a Fast Fourier Transform on said signal with said controller;
    analyzing said Fast Fourier Transform to determine a heart rate of a patient positioned on said support, said analyzing including dividing a harmonic peak of said Fast Fourier Transform by an integer greater than one that corresponds to said harmonic peak; and
    determining a breathing rate of the patient with the controller based upon said signal.

23. The method of claim 22 wherein said support includes a surface of a bed that supports an entire weight of the patient.

24. The method of claim 23 further including using said signal from said force sensor to determine the patient's weight.

25. The method of claim 24 wherein said determining of a breathing rate of the patient includes analyzing said Fast Fourier Transform.

26. The method of claim 24 further including determining whether the patient is experiencing a seizure or not from said signal.

27. The method of claim 22 further including low-pass filtering said signal prior to performing said Fast Fourier Transform.

28. A method of collecting data about a patient comprising:
providing a support deck adapted to support a patient, said support deck including a plurality of sections pivotable with respect to each other such that a position of a patient's body supported on said support deck may be changed;
providing a load frame supporting said support deck, and said load frame remaining generally stationary and flat as said sections of said support deck are pivoted with respect to each other;
providing a force sensor in contact with said load frame, said force sensor sensing a force exerted by said load frame on said force sensor, said force sensor generating a signal corresponding to said force;
providing a controller in communication with said force sensor;
performing a Fast Fourier Transform on said signal with said controller;
analyzing said Fast Fourier Transform to determine a heart rate of a patient positioned on said support; and
determining a breathing rate of the patient with the controller based upon said signal.

29. A method of monitoring a condition of a patient comprising:
providing a support deck adapted to support a patient's weight, said support deck including a plurality of sections pivotable with respect to each other such that a position of a patient's body supported on said support deck may be changed;
providing a load frame adapted to support said support deck, said load frame remaining generally stationary and flat as said sections of said support deck are pivoted with respect to each other;
providing an intermediate frame adapted to support said load frame;
providing a plurality of force sensors that sense forces exerted by said support deck on each of said force sensors, said force sensors generating signals corresponding to said forces;
providing a controller in communication with said force sensors; and
determining at least one of a heart rate, a breathing rate, and a seizure status of the patient from said signals using said controller.

30. The method of claim 29 further including performing a Fast Fourier Transform on at least one of said signals and determining from said Fast Fourier Transform at least one of said heart rate and breathing rate.

31. The method of claim 30 further including:
performing a second Fast Fourier Transform on said Fast Fourier Transform; and
using said second Fast Fourier Transform to determine at least one the heart rate and the breathing rate of the patient.

32. The method of claim 29 further including:
performing a first Fast Fourier Transform on a first one of said signals;
performing a second Fast Fourier Transform on a second one of said signals; and
using said second Past Fourier Transform and said first Fast Fourier Transform to determine at least one of the heart rate and the breathing rate of the patient.

33. A method of analyzing forces exerted by a patient, said method comprising:
providing a support deck adapted to support a patient's weight, said support deck including a plurality of sections pivotable with respect to each other such that a position of a patient's body supported on said support deck may be changed;
providing a load frame adapted to support said support deck, said load frame remaining generally stationary and flat as said sections of said support deck are pivoted with respect to each other;
providing a force sensor that senses a force exerted by said load frame onto said force sensor, said force sensor generating a signal corresponding to said force;
providing a controller in communication with said force sensor;
processing said signal using said controller to produce a processed output;
using a second sensor different from said force sensor to determine at least one of a patient's breathing rate and heart rate; and
determining a correlation between said processed output and said at least one of the patient's breathing rate and heart rate determined by said second sensor.

34. The method of claim 33 further including storing said correlation in an electronic memory for future use in situations where said second sensor is not used.

35. The method of claim 34 wherein said processing includes performing a Fast Fourier Transform on said signal.

36. A patient support apparatus comprising:
a support adapted to at least partially support a weight of a patient;
a force sensor adapted to detect a force exerted from said support onto said force sensor, said force sensor outputting a signal corresponding to said force; and
a controller in communication with said force sensor, said controller adapted to calculate a Fast Fourier Transform of said signal and use said Fast Fourier Transform to determine a heart rate of a patient positioned on said support, said controller determining said heart rate by identifying a harmonic peak in said Fast Fourier Transform and dividing said harmonic peak by an integer greater than one that corresponds to said harmonic peak.

37. The apparatus of claim 36 wherein said controller analyzes a plurality of peaks in said Fast Fourier Transform to determine the heart rate, said plurality of peaks located at integer multiples of the heart rate.

38. A patient support apparatus comprising:
a support deck adapted to support a patient, said support deck including a plurality of sections pivotable with respect to each other such that a position of a patient's body supported on said support deck may be changed;
a load frame supporting said support deck;
a first force sensor adapted to detect a force exerted from said load frame onto said first force sensor, said first force sensor outputting a first signal corresponding to said force; and
a second force sensor adapted to detect a second force exerted from said load frame onto said second force sensor, said second force sensor outputting a second signal corresponding to said second force; and a controller in communication with said first and second force sensors, said controller adapted to determine from said first and second signals at least one of a breathing rate and heart rate of a patient positioned on said support, said controller adapted to determine said at least one of a breathing rate and a heart rate by calculating a Fast Fourier Transform of at least one of said first signal, said second signal, or a combination of said first and second signals.

39. The method of claim 28 further including using said signal from said force sensor to determine the patient's weight.

* * * * *

UNITED STATES PATENT AND TRADEMARK OFFICE
CERTIFICATE OF CORRECTION

PATENT NO. : 7,699,784 B2  Page 1 of 1
APPLICATION NO. : 11/773714
DATED : April 20, 2010
INVENTOR(S) : David Kim Soui Wan Fong and Jean-Paul Dionne It is certified that error appears in the above-identified patent and that said Letters Patent is hereby corrected as shown below:

Column 14
Claim 32, Line 6, "Past" should be --Fast--

Signed and Sealed this

Sixteenth Day of November, 2010

David J. Kappos
*Director of the United States Patent and Trademark Office*